US010791929B2

(12) United States Patent
Duesterhoft et al.

(10) Patent No.: US 10,791,929 B2
(45) Date of Patent: Oct. 6, 2020

(54) SYSTEMS AND METHODS FOR MONITORING COMPRESSION WITH COMPRESSION BANDAGES HAVING STRETCHABLE ELECTRONICS

(71) Applicant: Elwha LLC, Bellevue, WA (US)

(72) Inventors: Paul Duesterhoft, Grapevine, TX (US); Roderick A. Hyde, Redmond, WA (US); Gary L. McKnight, Bothell, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 490 days.

(21) Appl. No.: 15/174,269

(22) Filed: Jun. 6, 2016

(65) Prior Publication Data

US 2017/0348155 A1 Dec. 7, 2017

(51) Int. Cl.
*A61F 13/00* (2006.01)
*A61B 5/00* (2006.01)
(Continued)

(52) U.S. Cl.
CPC .......... *A61B 5/0002* (2013.01); *A61B 5/6831* (2013.01); *A61F 13/00038* (2013.01);
(Continued)

(58) Field of Classification Search
CPC .......... A61H 2201/5074; A61B 5/7221; A61B 2562/0266; A61B 2562/028;
(Continued)

(56) References Cited

U.S. PATENT DOCUMENTS

| 5,218,954 A | 6/1993 | van Bemmelen |
| 5,546,955 A * | 8/1996 | Wilk ...................... A61B 5/015 600/549 |

(Continued)

FOREIGN PATENT DOCUMENTS

| WO | 03060449 A1 | 7/2003 |
| WO | 2005067796 A1 | 7/2005 |

(Continued)

OTHER PUBLICATIONS

PCT International Search Report; International App. No. PCT/US2017/036072; dated Sep. 8, 2017; pp. 1-4.
(Continued)

*Primary Examiner* — Kim M Lewis
(74) *Attorney, Agent, or Firm* — Daniel J. Honz; Advent, LLP

(57) ABSTRACT

Systems and methods are described for monitoring compression applied by a compression bandage to a body portion of an individual. A system embodiment includes, but is not limited to, a deformable substrate integrated with a textile configured to conform to a body portion; a sensor assembly coupled to the deformable substrate, the sensor assembly including one or more strain gauges configured to generate one or more sense signals associated with a strain of the textile; circuitry operably coupled to the sensor assembly and configured to receive the one or more sense signals associated with the strain of the textile; and a reporter operably coupled to the circuitry and configured to generate one or more communication signals responsive to instruction by the circuitry, the one or more communication signals associated with the strain of the textile.

20 Claims, 14 Drawing Sheets

(51) Int. Cl.
*A61F 13/06* (2006.01)
*A61F 13/08* (2006.01)

(52) U.S. Cl.
CPC ...... *A61F 13/00051* (2013.01); *A61F 13/064* (2013.01); *A61F 13/08* (2013.01); *A61B 5/6829* (2013.01); *A61B 2562/0257* (2013.01); *A61B 2562/0261* (2013.01); *A61B 2562/0285* (2013.01); *A61B 2562/043* (2013.01); *A61F 2013/0028* (2013.01); *A61F 2013/00123* (2013.01)

(58) Field of Classification Search
CPC .... A61B 2562/0252; A61B 2562/0247; A61B 5/1117; A61B 2562/0219; A61B 2562/0261; A61B 5/6804; A61B 5/1118; A61B 5/1122; A61B 5/6823; A61B 5/6831; A61B 5/0826; A61B 5/113; A61B 5/4818; A61B 5/6814; A61B 2562/0257; A61B 2562/0285; A61B 2562/043; A61B 2562/046; A61B 2562/164; A61B 5/0002; A61B 5/03; A61B 5/0488; A61B 5/04882; A61B 5/0492; A61B 5/1073; A61B 5/4343; A61B 5/4356; A61B 5/6805; A61B 5/6824; A61B 5/6829; A61B 5/6852; A61B 5/7455; A61B 10/02; A61B 17/0218; A61B 17/3205; A61B 17/3207; A61B 1/32; A61B 2017/00566; A61B 2017/00876; A61B 2017/0212; A61B 2017/22084
USPC .......................................................... 602/60
See application file for complete search history.

(56) References Cited

U.S. PATENT DOCUMENTS

| | | | |
|---|---|---|---|
| 6,135,116 A | 10/2000 | Vogel et al. | |
| 6,809,462 B2 | 10/2004 | Pelrine et al. | |
| 7,413,802 B2 | 8/2008 | Karayianni et al. | |
| 7,687,678 B2 | 3/2010 | Jacobs | |
| 7,878,030 B2 | 2/2011 | Burr | |
| 7,956,233 B2 | 6/2011 | Lecomte et al. | |
| 8,013,750 B2 | 9/2011 | Sandholdt | |
| 8,025,632 B2 | 9/2011 | Einarsson | |
| 8,032,199 B2 * | 10/2011 | Linti ................. | A41D 13/1281 600/388 |
| 8,082,762 B2 | 12/2011 | Burr | |
| 2002/0086598 A1 | 7/2002 | Velpari et al. | |
| 2004/0180202 A1 | 9/2004 | Lawton et al. | |
| 2006/0078721 A1 | 4/2006 | Rau et al. | |
| 2007/0042179 A1 | 2/2007 | Karayianni et al. | |
| 2008/0143080 A1 | 6/2008 | Burr | |
| 2008/0281244 A1 | 11/2008 | Jacobs | |
| 2009/0112145 A1 | 4/2009 | Lecomte et al. | |
| 2010/0231377 A1 * | 9/2010 | Sandholdt ............... | A61B 5/03 340/539.1 |
| 2011/0015498 A1 | 1/2011 | Mestrovic et al. | |
| 2011/0067454 A1 | 3/2011 | Burr | |
| 2011/0282164 A1 | 11/2011 | Yang et al. | |
| 2011/0319787 A1 | 12/2011 | Lamoise et al. | |
| 2012/0229270 A1 * | 9/2012 | Morley .............. | A61B 5/02416 340/539.12 |
| 2014/0303452 A1 * | 10/2014 | Ghaffari ................... | A61B 1/05 600/301 |
| 2015/0031964 A1 * | 1/2015 | Bly ....................... | A61B 5/7465 600/301 |
| 2016/0015271 A1 * | 1/2016 | Wang ................... | A61B 5/0053 600/578 |
| 2016/0054185 A1 * | 2/2016 | Servati ................... | B82Y 10/00 73/774 |
| 2016/0120734 A1 * | 5/2016 | Ishikawa ................... | A45F 3/04 601/151 |
| 2016/0143534 A1 * | 5/2016 | Hyde ................. | A41D 13/1281 600/553 |
| 2016/0242964 A1 * | 8/2016 | Rapp .................. | A61F 13/00063 |
| 2017/0061766 A1 * | 3/2017 | Gu ....................... | G08B 21/0446 |
| 2017/0128306 A1 * | 5/2017 | Chase ..................... | A61F 13/04 |

FOREIGN PATENT DOCUMENTS

| | | |
|---|---|---|
| WO | 2007113430 | 10/2007 |
| WO | 2012093259 | 7/2012 |
| WO | 2016081400 A1 | 5/2016 |
| WO | WO 2016/081400 A1 | 5/2016 |

OTHER PUBLICATIONS

STretchable ELectronics for Large Area applications (STELLA), Steinbrunn, Final Status of the URGO band aid demonstrator, Issue No. VI, p. 2 (2010).
Pressure Mapping of Medical Compression Bandages Used for Venous Leg Ulcer Treatment, Al Khaburi, Jawad Ameen Jawad (2010).
http://www.bizjournals.com/seattle/blog/techflash/2013/05/connected-feet-local-startup-weaves.html (Parkhurst, Emily, 2013).
Edema Stocking Whitepaper (2013).
Effect of elastic compression stockings in patients with varicose veins and healthy controls measured by strain gauge plethysmography, Hirai et al., Skin Res Technol. 2002; 8:236-239.
http://www.worldwidewounds.com/1997/september/Thomas-Bandaging/bandage-paper.html (Thomas, Stephen, 1997).
http://phys.org/news/2012-07-ultra-sensitive-artificial-skin.html.
Epidermal Electronics, Kim et al., Science 333, 838 (2011).
Conformal piezoelectric systems for clinical and experimental characterization of soft tissue biomechanics (Nature Materials, Dagdeviren et al., vol. 14 (2015)).
Recent Advances in Flexible Sensors for Wearable and Implantable Devices (Journal of Applied Polymer Science, Pang et al., 130: 1429-1441 (2013)).
Stretchable Electronics: Materials Strategies and Devices (Advanced Materials, Kim et al., 2008, 20, 4887-4892 (2008)).
Soft Sensors Map Skin Mechanics, Davenport, Chemical & Engineering News, vol. 93 Issue 21, p. 10 (2015).
Performance of Epidermal RFID Dual-loop Tag and On-Skin Retuning, Amendola et al., IEEE Transactions on Antennas and Propagation, vol. 63, No. 8 (2015).
Miniaturized Flexible Electronic Systems with Wireless Power and Near-Field Communication Capabilities, Kim et al., Advanced Functional Materials, 25, 4761-4767 (2015).
Multifunctional Epidermal Electronics Printed Directly Onto the Skin, Yeo et al., Advanced Materials, DOI: 10.1002/adma. 201204426 (2013).
Electronics for the Human Body, Rogers, JAMA, vol. 313, No. 6 (2015).
European Patent Office, Extended European Search Report, Pursuant to Rule 62 EPC; App. No. EP 17810822.1; Jan. 23, 2020; pp. 1-6.
Written Opinion dated Apr. 6, 2020 for App. No. 11201810908X.

* cited by examiner

SYSTEMS AND METHODS FOR MONITORING COMPRESSION WITH COMPRESSION BANDAGES HAVING STRETCHABLE ELECTRONICS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a compression bandage system includes, but is not limited to, a deformable substrate integrated with a textile configured to conform to a skin surface of a body portion; a sensor assembly coupled to the deformable substrate, the sensor assembly including one or more strain gauges configured to generate one or more sense signals associated with a strain of the textile; circuitry operably coupled to the sensor assembly and configured to receive the one or more sense signals associated with the strain of the textile; and a reporter operably coupled to the circuitry and configured to generate one or more communication signals responsive to instruction by the circuitry, the one or more communication signals associated with the strain of the textile.

In an aspect, a method includes, but is not limited to, applying compression to a body portion of an individual subject via a compression bandage, the compression bandage including a textile having a sensor assembly integrated therewith; generating one or more sense signals via the sensor assembly, the one or more sense signals associated with a strain of the textile; and reporting one or more communication signals associated with the strain of the textile responsive to instruction by circuitry coupled with the sensor assembly.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
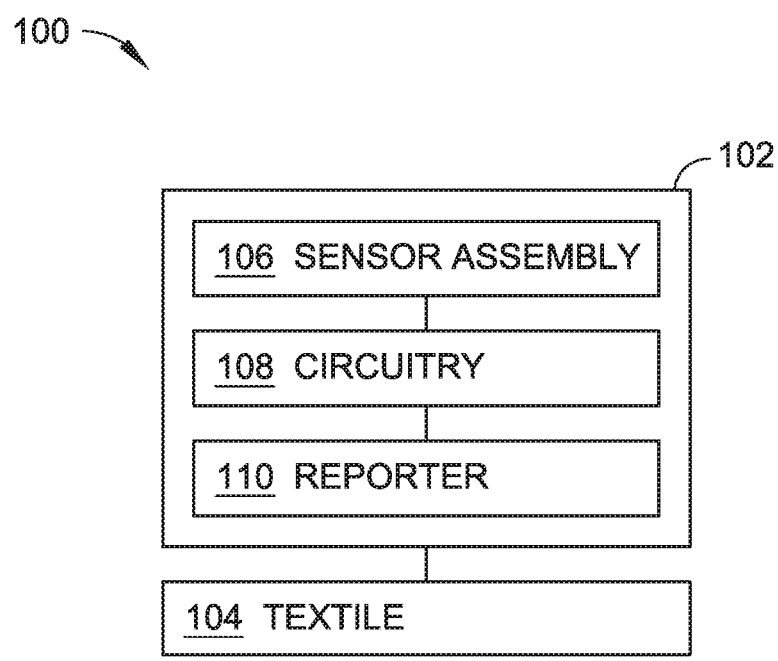
FIG. 1 is a schematic of a compression bandage system for monitoring compression applied by a compression bandage having stretchable electronics integrated therewith.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems and methods are described for monitoring compression applied by a compression bandage to a body portion of an individual subject. Such systems and methods can employ compression bandages having stretchable electronics integrated with a textile of the compression bandage to monitor one or more features of the compression bandage to aid in ensuring that a proper compression is applied to the body portion. For example, such systems and methods can monitor strains associated with the textile of a compression bandage applied to the body portion of the individual subject, where such strains can provide an indication as to the level of compression being applied to the body portion via the compression bandage. Compression bandages are available to both medical and non-medical personnel in a variety of forms and for use in multiple contexts. One form is termed long-stretch compression bandages that may be comprised of elastic fibers to allow the bandage to significantly stretch (e.g., about 140% to about 300% of the bandage's original length). Little working pressure is provided by long-stretch bandages, which means little resistance is exerted by the bandage during muscle contractions.

Another form of compression bandages, termed short-stretch, have been used by medical personnel, including physical therapists and occupational therapists, for treatment of edema, lymphedema, and venous conditions, such as venous ulcers. Short-stretch bandages generally provide less stretchability than long-stretch bandages. For example, short-stretch bandages can stretch from about 30% to about 60% of the bandage's original length. When layered, short-stretch bandages cause a high working pressure, which can force blood to flow through the veins and toward the heart. Orthopedists may use compression bandages to restrict blood flow to a specific area in order to treat muscle strains and sprains (e.g., associated with sports injuries or other medical condition) and as a means to hold a splint and padding in place to treat a bone fracture. Medical and non-medical personnel may use compression bandages as an in-patient or home remedy for a variety of edema or vein-related issues or conditions. Medical and non-medical personnel may use compression bandages for wound care, as well. The composition of compression bandages may vary from latex, natural rubber, cotton, polyester, and latex-free elastic yarns. To keep compression bandages in place, a fastener, such as a metal clip, hook and loop tape, an adhesive, an adhesive tape, or the like, may be used. Such fasteners may be detachable from the compression bandage or integral to the compression bandage. Alternatively, the bandage can be applied without an additional fastener. In an embodiment, the compression bandage can comprise a garment, for example a sleeve or a stocking. In an embodiment, the compression bandage can comprise a brace.

In embodiments, the systems and methods described herein employ a deformable substrate integrated with a textile, such as a textile of a compression bandage. The deformable substrate is configured to accommodate the flexibility and stretchability of the compression bandage. The deformable substrate is configured to conform to a contour of a body portion, e.g., the curvature of a limb. The deformable substrate can include, but is not limited to, a polymer, a membrane, or a film. For example, the deformable substrate can include an elastomeric polymer, a hydrocolloid film, a silicon membrane, a gas-permeable elastomeric sheet, or combinations thereof. The deformable substrate can be integrated with the textile such that the textile supports the deformable substrate and corresponding components mounted thereto against the body portion when the textile is positioned proximate to (e.g., wrapped around or about) the body portion.

In embodiments, the systems and methods described herein employ a sensor assembly coupled to the deformable substrate to provide sensing of one or more conditions of the textile. For example, the systems and methods described herein can include one or more strain gauges configured to generate one or more sense signals associated with a strain of the textile. The strain measurements can provide an indication as to whether the textile is providing an appropriate level of pressure to the body portion. The sensor assembly can be structured relative to the deformable substrate such that at least a portion of the sensor assembly is embedded within the deformable substrate, affixed to the deformable substrate, residing on the deformable substrate, or a combination thereof. The sensor assembly can be structured relative to the textile such that at least a portion of the sensor assembly is embedded within the textile, woven into the textile, affixed to a surface of the textile, printed directly onto a surface of the textile, or a combination thereof. In embodiments, the sensor assembly is directly integrated with the textile, without support from an accompanying substrate. For example, the sensor assembly (e.g., associated strain gauges) can be printed directly onto a surface of the textile, embedded within the textile, woven into the textile, affixed to a surface of the textile, printed directly onto a surface of the textile, or a combination thereof without being coupled to an additional substrate. The sensor assembly can be reversibly affixed to at least one of the deformable substrate or the textile, such that the sensor assembly can be removable, reusable, disposable, or the like.

In embodiments, the systems and methods described herein employ a reporter to provide communication signals associated with strain of the textile. The reporter can be coupled with circuitry configured to process signals received from the sensor assembly, such as to determine whether a strain of the textile exceeds, meets, or is lower than a particular (e.g., threshold) strain value, to compare the signals to reference data, or the like. The reporter can convey information via the one or more communication signals, including but not limited to, an auditory indication of the information, a visual indication of the information, or a tactile indication of the information.

Figure 2:
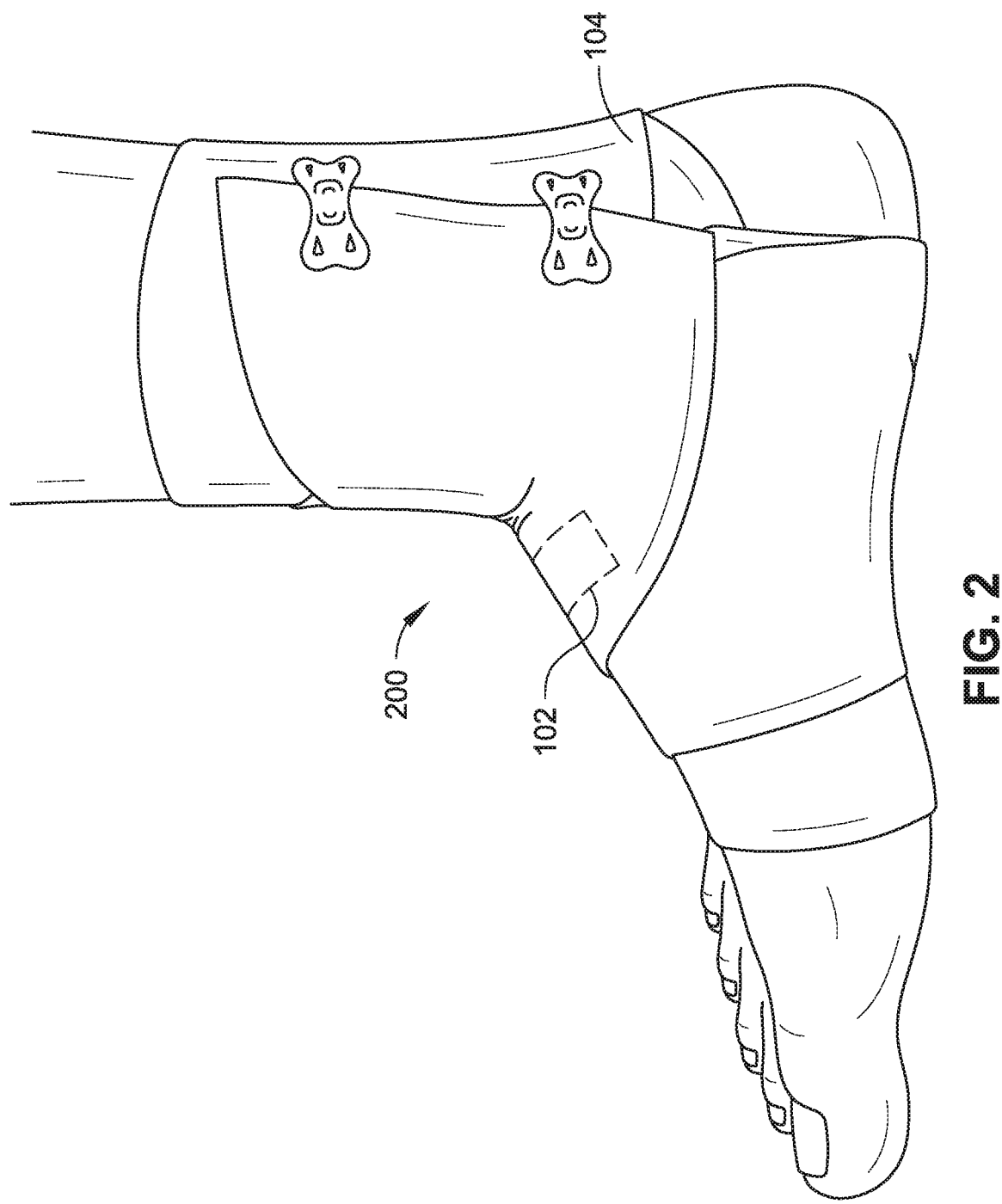
FIG. 2 is a schematic of an embodiment of a system such as shown in FIG. 1.

In embodiments, shown in FIG. 1, a compression bandage system (or device) 100 is configured to monitor a strain associated with a textile of a compression bandage to aid in managing treatment of an individual via the compression bandage, such as to ensure that proper pressure is being applied to a body portion of the individual via the compression bandage. The compression bandage system 100 includes a deformable substrate 102, a textile 104, a sensor assembly 106, system circuitry 108, and a reporter 110. The deformable substrate 102 is integrated with the textile 104 and is configured to conform to a body portion of an individual subject, such as by flexing, stretching, or otherwise accommodating, to the conformation of the textile 104 when applied to the body portion. For example, the deformable substrate 102 can comprise a deformable (e.g., conformable, flexible, stretchable, etc.) material configured to interface with, and conform to, a body portion of a human subject. The pliable nature (e.g., flexibility and stretchability) of the deformable substrate 102 facilitates interaction between the deformable substrate 102 and the associated textile 104, such as to permit conformation of the deformable substrate 102 with the textile 104, for example when the textile 104 is interacting with (e.g., wrapped around or about) the body portion. For example, when wrapped around a body portion, the textile 104 can stretch, bend, contract, deform, or the like, such as during movement of the body portion, and the deformable substrate 102 can conform to these modifications in the textile 104 shape, size, position, etc. FIG. 2 shows an embodiment where the textile 104 is wrapped about an ankle region 200 of an individual. The deformable substrate 102 is integrated with the textile 104 and can adapt to changes in the textile 104 during motion of the leg, ankle, or foot of the individual. While FIG. 2 shows a single deformable substrate 102 integrated with the textile 104, the compression bandage system 100 can utilize more than one deformable substrate 102 integrated with the textile 104, such as to position differing deformable substrates 102 around different portions of the ankle region 200 (or other body portion) when the textile is applied to the individual. The deformable substrate 102 or the sensor assembly 106 can be positioned or integrated on a portion of the textile, such that the deformable substrate 102 and/or sensor assembly 106 occupies a footprint that is less than the surface area of the textile 104. In embodiments, the deformable substrate 102 or the sensor assembly 106 can be positioned or integrated across one or more of the entire length of the textile 104 or the entire width of the textile 104.

In embodiments, the deformable substrate 102 can include one or more of a stretchable/flexible fabric, paper, polymer (e.g., an elastomeric polymer, polyimide, polyvinyl, an organic polymer such as PDMS, xylylene, parylene, an inorganic polymer, biopolymer, a composite material or any combination of these), a film (e.g. a hydrocolloid film), a membrane (e.g., silicon membrane), a gas-permeable elastomeric sheet, or other deformable (e.g., stretchable, flexible, or pliable) material. In an embodiment, at least one of the sensor assembly 106, the circuitry 108, or the reporter 110 resides on the deformable substrate 102, such as residing on at least a portion of one or more of a stretchable/flexible fabric, an elastomeric polymer, a hydrocolloid film, a membrane (e.g., silicon membrane), a gas-permeable elastomeric sheet, or other deformable material. In an embodiment, at least one of the sensor assembly 106, the circuitry 108, or the reporter 110 is embedded within the deformable substrate 102, such as embedded within at least a portion of one or more of a stretchable/flexible fabric, an elastomeric polymer, a hydrocolloid film, a membrane (e.g., silicon nanomembrane), a gas-permeable elastomeric sheet, or other deformable material.

Figure 3:
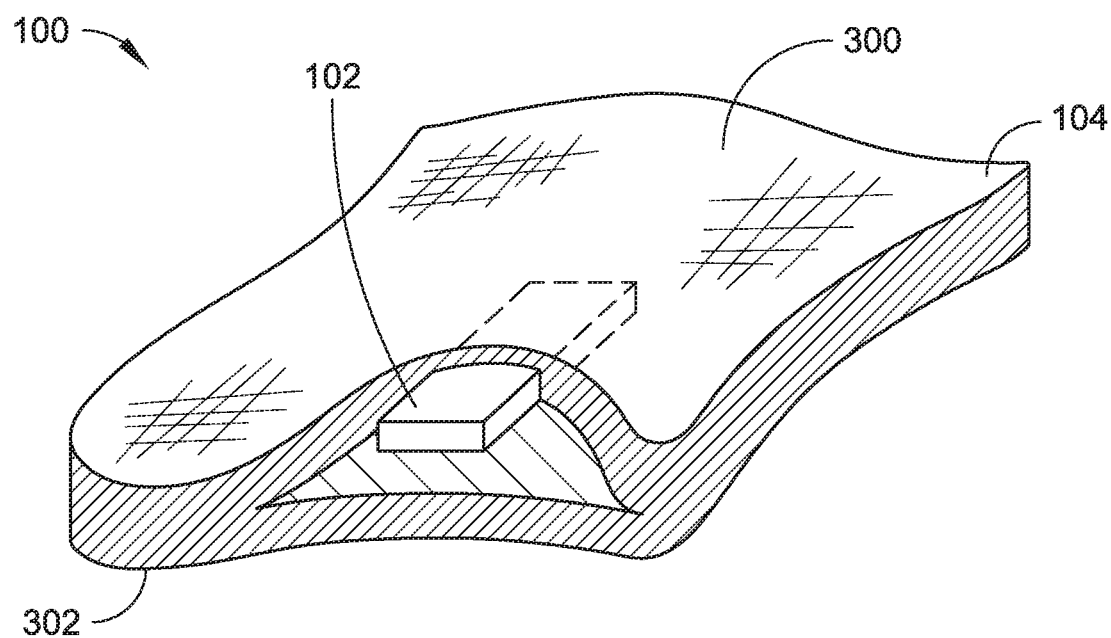
FIG. 3 is a schematic of an embodiment of a system such as shown in FIG. 1.
Figure 4A:
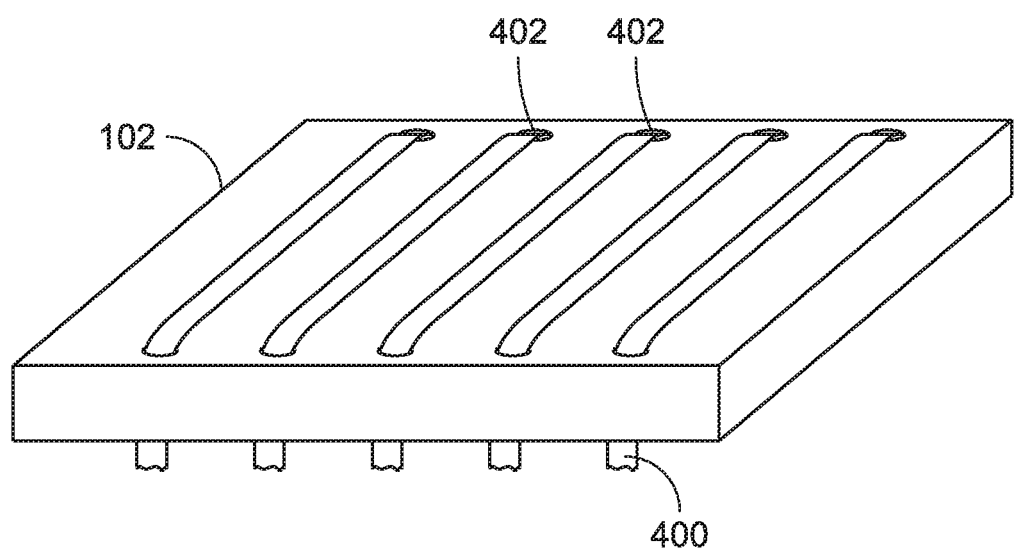
FIG. 4A is a schematic of an embodiment of a system such as shown in FIG. 1.
Figure 4B:
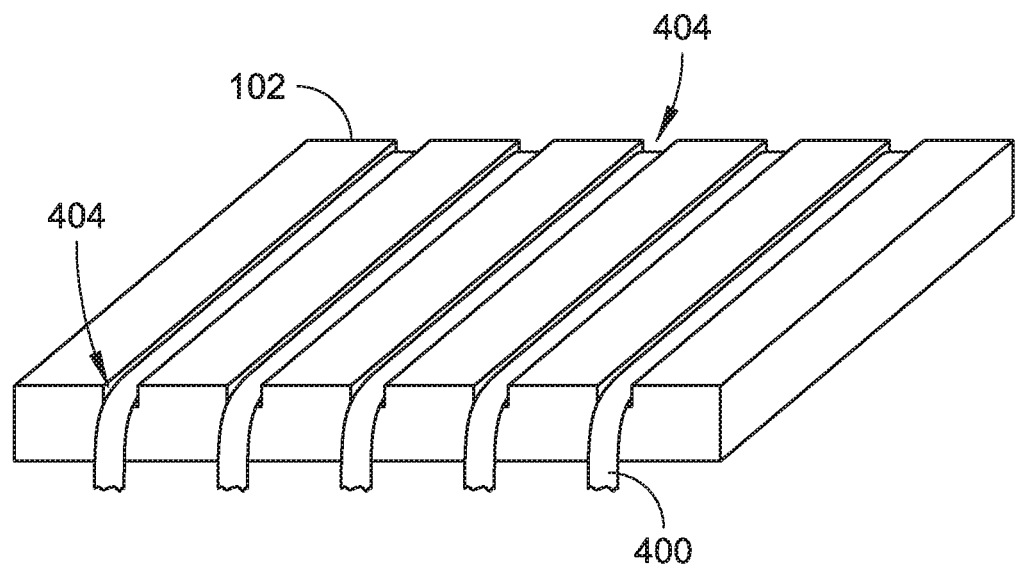
FIG. 4B is a schematic of an embodiment of a system such as shown in FIG. 1.
Figure 4C:
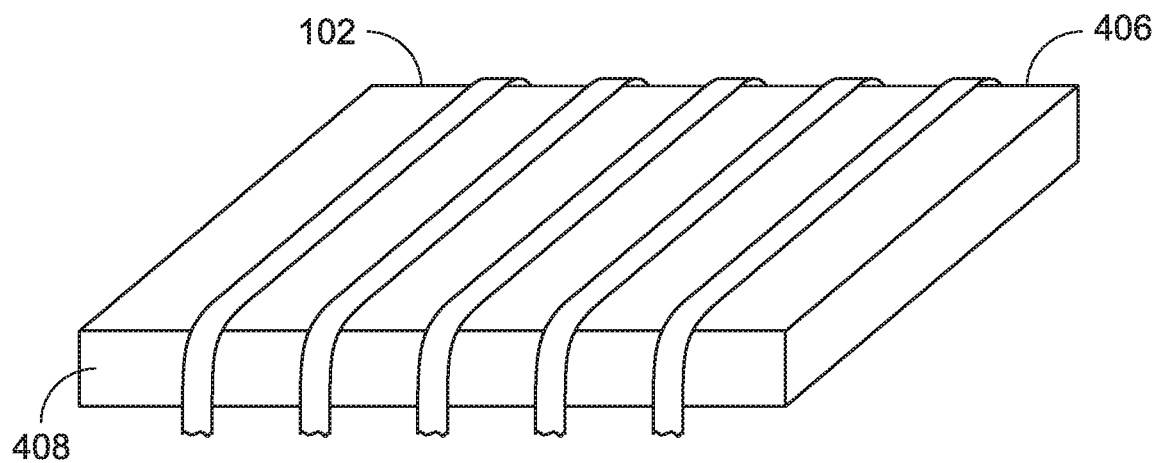
FIG. 4C is a schematic of an embodiment of a system such as shown in FIG. 1.

The deformable substrate 102 can be integrated with the textile 104 based on a threading configuration, a weave pattern, or the like to secure the deformable substrate 102 relative to the textile 104. For example, in an embodiment, shown in FIG. 3, the textile 104 includes an inner surface 300 and an outer surface 302, wherein at least a portion of the deformable substrate 102 is positioned between the inner surface 300 and the outer surface 302. The inner surface 300 can be configured to be adjacent the body portion when the textile 104 is positioned proximate to the body portion, such as wrapped around the body portion to provide compression. In embodiments, the deformable substrate can be attached, adhered, or mounted to the inner surface 300 or to the outer surface 302. The deformable substrate 102 can be attached via an adhesive material, via one or more threads or fibers of the textile 104, or other binding technique. In embodiments, the deformable substrate 102 is integral to a weave of the textile 104, whereby one or more fiber or thread of the textile can secure the deformable substrate 102 to or within the textile 104. For example, as shown in FIGS. 4A through 4C, the deformable substrate 102 can be integral to a weave of the textile 104 or bound to the textile 104 via interaction between one or more threads (or fibers) 400 of the textile 104 with one or more corresponding apertures 402 formed in the deformable substrate 102 (shown in FIG. 4A), via interaction between one or more threads (or fibers) 400 of the textile 104 with one or more corresponding channels or grooves 404 formed by the deformable substrate 102 (shown in FIG. 4B), via interaction between one or more threads (or fibers) 400 of the textile 104 with one or more surfaces (e.g., top surface 406, side surface 408, and so forth) of the deformable substrate 102 (shown in FIG. 4C), or via a combination of integrations.

In embodiments, the textile 104 includes one or more electronic or conductive threads that incorporate one or more conductive materials (e.g., metallic, semi-conductive) to facilitate transfer of electric transmissions throughout at least a portion of the textile 104. The electronic threads can be integrated within a weave pattern of the textile 104, such that fabric threads are woven with electronic threads to form at least a portion of the textile 104. In embodiments, the electronic threads can facilitate transfer of electric transmissions between the textile 104 and one or more components coupled to the deformable substrate 102.

In embodiments, the compression bandage system 100, includes at least one flexible or stretchable electronic component. For example, at least one of the sensor assembly 106 (e.g., strain gauges as described herein), the circuitry 108, or the reporter 110 can include or be formed of flexible or stretchable electronics coupled to the deformable substrate 102. For example, interconnects (not illustrated) between these components or within the circuitry can include or be formed of flexible or stretchable electronics (e.g., serpentine conducting tracings allowing for stretchable interconnects) and coupled to the deformable substrate 102. For example, a power source (e.g., power source 1102 described herein), can include or be formed of flexible or stretchable electronics and be coupled to the deformable substrate 102. In embodiments, the at least one flexible or stretchable electronic component includes at least one of a wavy, bent, mesh (e.g., open mesh), buckled, or serpentine geometry. In embodiments, the at least one flexible or stretchable electronic component includes at least one nanowire, at least one nanoribbon, or at least one nanomembrane. In one implementation, the compression bandage system 100 includes one or more multifunctional electronic units comprising a stretchable/flexible system including a sensor assembly (e.g., sensor assembly 106), reporter (e.g., reporter 110), and power source (e.g., power source 1102) in communication via associated circuitry (e.g., circuitry 108), including interconnects, residing in or on a deformable substrate (e.g., deformable substrate 102) and integrated with a textile (e.g., textile 104).

In embodiments, the compression bandage system 100 can include at least one ultrathin electronic component. For example, an ultrathin (e.g., less than 20 micrometers) electronic component can include a thinned wafer (e.g., thinned silicon wafer bonded to a polymer substrate), an ultrathin chip, or the like. For example, ultrathin circuitry can include conductive layers formed on a deformable substrate (e.g., deformable substrate 102) such as parylene by evaporation deposition with UV lithography and etching. For example, at least one of the sensor assembly 106, the circuitry 108, or the reporter 110 can include ultrathin electronics.

In embodiments, the compression bandage system 100 can include at least one electrically conductive thread, yarn, or textile. For example, the sensor assembly 106, the circuitry 108, or the reporter 110 may include at least one electrically conductive thread or yarn. Electrically conductive threads, yarns, or textiles can be configured to provide sufficient current to induce at least one of a wired or wireless coupling, e.g., between electronic components. For example, electronically conductive threads, yarns, or textiles may form circuitry 108 configured to function in communication between one or more sensor assemblies 106, one or more reporters 110, or other circuitry 108. For example, electronically conductive threads, yarns, or textiles may form circuitry 108 configured to function in communication between a plurality of multifunctional electronic units each comprising one or more sensor assemblies, one or more reporters 110, and circuitry 108. Electrically conductive fibers, threads, and yarns can include a metallic material, semi-metallic material, semi-insulative material, semi-conductive material (e.g., silicon and a gallium arsenide), or transparent conductive material (e.g., an indium-tin-oxide (ITO) material). Electrical threads or yarns can be embedded in textiles using weaving, knitting or embroidery, for example, or can be attached using nonwoven production techniques such as adhesion. For example, electrically conductive yarns having curved configuration can be attached to an elastic textile (e.g., by sewing or by adhesion) and can form all or part of a sensor assembly 106 that measures strain, e.g., as the curved configuration is altered.

Figure 5:
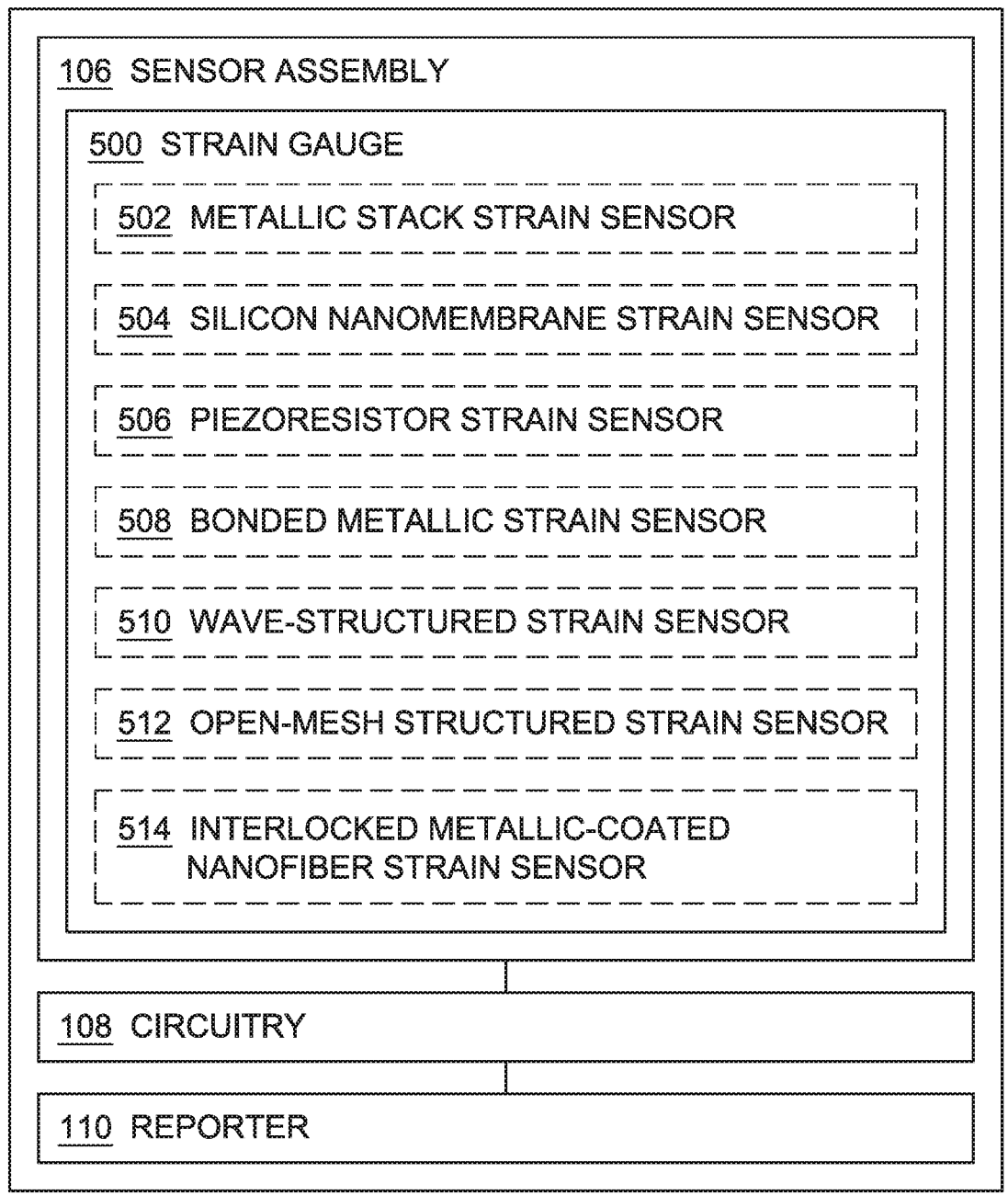
FIG. 5 is a schematic of an embodiment of a system such as shown in FIG. 1.

The sensor assembly 106 is coupled to the deformable substrate 102 and is positioned to generate one or more sense signals associated with a characteristic of the textile 104. For example, in an embodiment, shown in FIG. 5, the sensor assembly 106 includes one or more strain gauges 500 configured to generate one or more sense signals associated with a strain of the textile 104. The strain of the textile 104 can provide an indication that the associated compression bandage is not applied properly (e.g., providing too much pressure to the body portion, not providing enough pressure to the body portion, providing uneven pressure, etc.), or can provide an indication pertaining to the mechanical properties of the textile 104 (e.g., the textile 104 is becoming worn out, due for replacement, etc.), or can provide other indications. The strain gauge 500 can include, but is not limited to, one or more of a metallic stack strain sensor 502, a silicon nanomembrane strain sensor 504, a piezoresistor strain sensor 506, a bonded metallic strain sensor 508, a wave-structured strain sensor 510, an open-mesh structured strain sensor 512, an interlocked metallic-coated nanofiber strain sensor 514, or the like.

In embodiments, electronic components can be positioned directly adjacent to the bandage. For example, the electronic components (e.g., portions of the sensor assembly 106, the circuitry 108, the reporter 110, etc.) can be positioned between the textile 104 and the deformable substrate 102. In one example, electronics are printed directly on the textile 104 or are printed on a silicon wafer and are transferred (e.g., via a transfer substrate) to the textile 104, and the deformable substrate 102 is a film pasted or sprayed over the electronics. In an embodiment, the electronic components are encapsulated, for example between distinct deformable substrates 102 (e.g., a polymer and a film).

The metallic stack strain sensor 502 can include a first metallic material positioned on a second metallic material, where differences between electrical resistivity between the first metallic material and the second metallic material experienced during flexing or bending of the materials while mounted to a surface of interest can provide an indication of strain experienced by the surface. For example, in an embodiment, the metallic stack strain sensor 502 includes a titanium/gold stack (Ti/Au) stack with a thickness of 10 nanometers of titanium per 60 nanometers of gold. The Ti/Au stack can provide an electrical resistance of between about 305 ohms and 330 ohms for a strain percentage of between about 0.5% and 3.0%, which can be used to associate the change in electrical resistance of the stack to a strain experienced by the textile 104, which can correlate to a pressure applied by the textile 104 to the body portion.

Figure 6A:
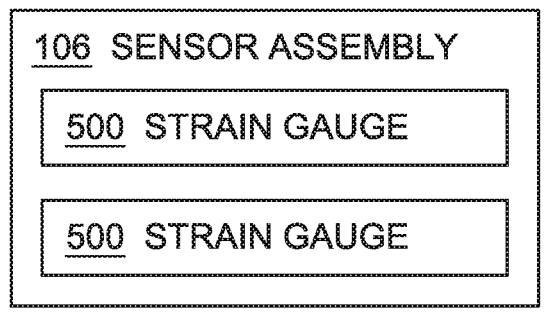
FIG. 6A is a schematic of an embodiment of a system such as shown in FIG. 1.
Figure 6B:
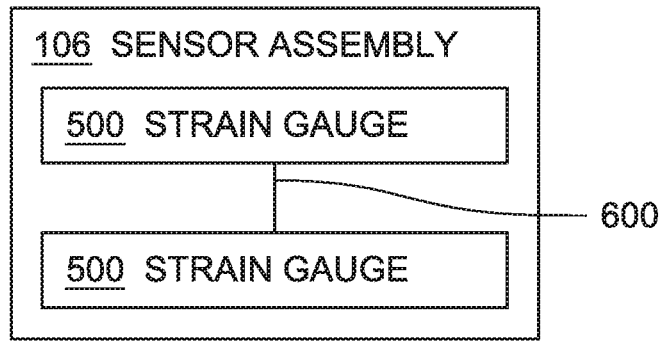
FIG. 6B is a schematic of an embodiment of a system such as shown in FIG. 1.
Figure 6C:
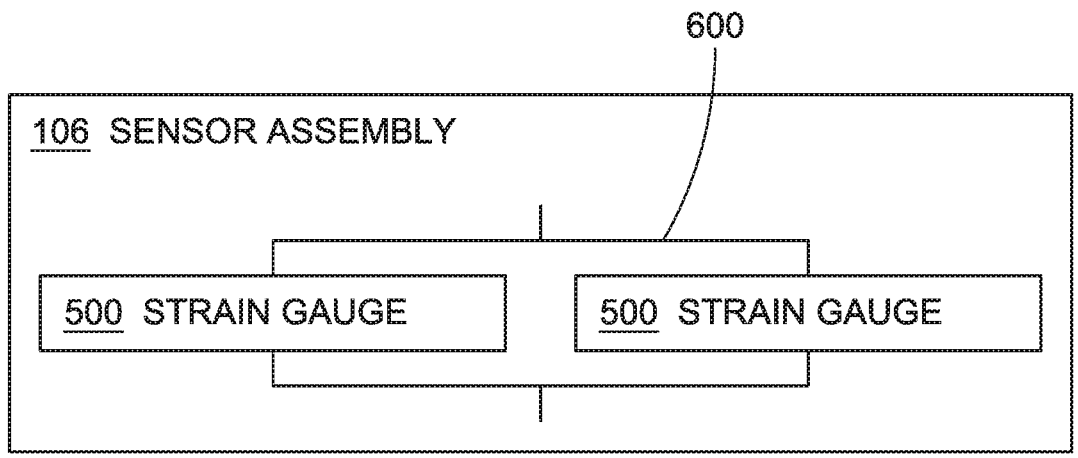
FIG. 6C is a schematic of an embodiment of a system such as shown in FIG. 1.
Figure 6D:
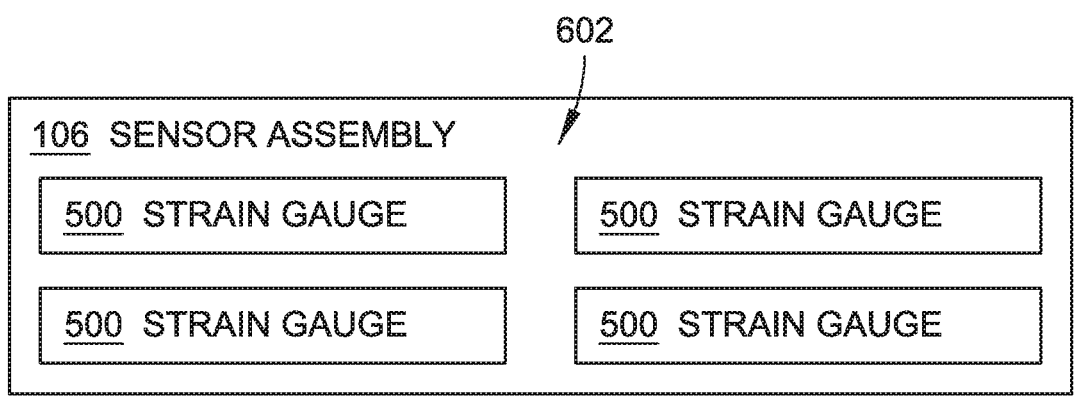
FIG. 6D is a schematic of an embodiment of a system such as shown in FIG. 1.

The silicon nanomembrane strain sensor 504 can include a thin strip of silicon to provide a thin crystalline semiconductor strip, where changes in the relative resistance of the silicon nanomembrane experienced during flexing or bending of the silicon while mounted to a surface of interest can provide an indication of strain experienced by the surface. For example, in an embodiment, the silicon nanomembrane strain sensor 504 includes a silicon nanomembrane having a thickness from about 100 nm to about 400 nm, a width from about 10 μm to about 100 μm, and a length from about 100 μm to about 1000 μm. Multiple strips of silicon nanomembrane can be utilized to monitor strain associated with the textile 104 along differing axes, such as by employing a silicon nanomembrane along a longitudinal axis of the textile 104 and employing a silicon nanomembrane along a transverse axis of the textile 104 (e.g., the longest dimension of the silicon nanomembrane being parallel to the respective axis). For example, the silicon nanomembranes can be arranged in an array (e.g., as described with respect to FIG. 6D).

The piezoresistor strain sensor 506 can include a material that generates electricity upon deformation. In an embodiment, the piezoresistor strain sensor 506 includes strip of material (e.g., a silicon nanomembrane, semiconducting material, metallic material, etc.) that tapers near a midpoint of the material (e.g., to provide a "dog-bone" shaped structure) that provides a change in electrical resistance upon experiencing mechanical strain (e.g., bending, flexing, etc.). For example, the piezoresistor strain sensor 506 can include a tapered silicon nanomembrane coupled to the textile 104 to associate the generated electricity of the silicon nanomembrane to a strain experienced by the textile 104. In an embodiment, the piezoresistor strain sensor 506 includes a nanoribbon of lead zirconate titanate (PZT) coupled between gold and platinum electrodes, where the nanoribbon generates electricity upon deformation. For example, in an embodiment, the piezoresistor strain sensor 506 includes a lead zirconate titanate nanoribbon coupled to the textile 104 to associate the generated electricity of the nanoribbon to a strain experienced by the textile 104.

The bonded metallic strain sensor 508 can include a metallic material arranged in a grid on a substrate. The metallic material can be structured as a fine wire or foil. In an embodiment, at least a portion of the grid is affixed directly to the textile 104. The grid can exhibit a linear change in electrical resistance upon experiencing mechanical strain (e.g., bending, flexing, etc.) For example, in an embodiment, the bonded metallic strain sensor 508 is applied to the textile 104 to associate the change in electrical resistance of the metallic grid to a strain experienced by the textile 104.

The wave-structured strain sensor 510 can include a relatively brittle wave-structured material (e.g., single-crystalline silicon) bonded on an elastic support material. In an embodiment, the wave-structured material includes a substantially planar base layer to mechanically couple to the elastic support material in a substantially continuous manner. In an embodiment, the wave-structured material mechanically couples to elastic support material at discontinuous bonding portions (e.g., at a "valley" of a wave). The wave-structured material can be micro-scale or nano-scale structures (e.g., ribbons, membranes, wires, etc.), where amplitudes and wavelengths of the wave-structure material can change in response to mechanical strains. For example, in an embodiment, the wave-structured strain sensor 510 is applied to the textile 104 to associate the change in electrical resistance of the wave-structured material to a strain experienced by the textile 104.

The open-mesh structured strain sensor 512 includes an open-mesh material having mesh connections at bridging elements, which can provide in-plane rotations of the mesh material(s) upon experiencing mechanical strain (e.g., bending, flexing, etc.). Tensile strains can be applied to ends of the open-mesh material to cause in-plane rotations at the bridging elements, which can alter a shape of the openings within the mesh (e.g., transitioning between open squares and open rhombuses). For example, strains applied in a direction not aligned to connecting bridges of the open-mesh material can lead to rotation of the connecting bridges about the connection points, providing a stretchable strain sensor. In an embodiment, the open-mesh structured strain sensor 512 is applied to the textile 104 to associate the change in electrical resistance of the open-mesh material to a strain experienced by the textile 104.

The interlocked metallic-coated nanofiber strain sensor 514 can include interlocked arrays of metallic-coated nanofibers, each array supported by a substrate material to providing differing levels of interconnection and electric resistance between the arrays when external strains are applied. For example, the interlocked metallic-coated nanofiber strain sensor 514, can include two arrays of high-aspect-ratio platinum-coated polymeric nanofibers each supported on a thin polydimethylsiloxane (PDMS) substrate, where when mechanical strain is applied, the degree of interconnection of the nanofibers and the electrical resistance of the sensor changes in a reversible, directional manner. In an embodiment, the interlocked metallic-coated nanofiber strain sensor 514 is applied to the textile 104 to associate the change in electrical resistance of the arrays to a strain experienced by the textile 104.

The sensor assembly 106 can be structured relative to the deformable substrate 102 such that at least a portion of the sensor assembly 106 is embedded within the deformable substrate 102, affixed to the deformable substrate 102, residing on the deformable substrate 102, or a combination thereof. For example, at least a portion of a strain gauge 500 can be embedded within the deformable substrate 102, can be affixed to the deformable substrate 102, can reside on the deformable substrate 102, or a combination thereof. The sensor assembly 106 can be structured relative to the textile 104 such that at least a portion of the sensor assembly 106 is embedded within the textile 104, woven into the textile 104, affixed to a surface of the textile 104, printed directly onto a surface of the textile 104, or a combination thereof. For example, at least a portion of a strain gauge 500 can be embedded within the textile 104, woven into the textile 104, affixed to a surface of the textile 104, printed directly onto a surface of the textile 104, or a combination thereof. The sensor assembly 106 can be reversibly affixed to at least one of the deformable substrate 102 or the textile 104, such that the sensor assembly 106 can be removable, reusable, disposable, or the like. For example, at least a portion of a strain gauge 500 can be reversibly affixed to at least one of the deformable substrate 102 or the textile 104, such that the strain gauge 500 can be removable, reusable, disposable, or the like.

The sensor assembly 106 can include a plurality of strain gauges 500 in various configurations. For example, the plurality of strain gauges 500 can be utilized to cover a large surface area, such as for a long or wide portion of textile 104, or can be utilized to monitor strain at different positions of the body portion (e.g., a first strain gauge at an ankle region, a second strain gauge at a lower leg region, a third strain gauge at a top of the foot; a first strain gauge at a wrist region, a second strain gauge at a top of the hand, a third strain gauge at a finger region, etc.), or a combination thereof. The plurality of strain gauges 500 can be utilized to monitor compression at different body portions to provide a gradient pressure treatment, for example, by monitoring compression at an ankle with a first strain gauge and monitoring compression at a knee with a second strain gauge. Such monitoring can facilitate determinations (e.g., via the circuitry 108) that a portion of the textile 104 is binding too tightly (e.g., the textile 104 has folded over widthwise), that there is uneven pressure exerted (e.g., when no gradient is desired), or whether the pressure gradient is within predetermined operation guidelines. In embodiments, the strain gauges 500 are interconnected or otherwise operably coupled to respective other strain gauges 500 via one or more electrically conductive threads, yarn, or textile (shown as 600). For example, the electrically conductive threads, yarn, or textile 600 can facilitate transfer of one or more of data signals, power, or the like between respective strain gauges 500. In embodiments, the electrically conductive threads, yarn, or textile 600 can be coupled between substrates supporting the strain gauges 500, such as if separate deformable substrates 102 are provided for respective strain gauges 500. In an embodiment, shown in FIG. 6A, the sensor assembly 106 includes a plurality of strain gauges 500 arranged in tandem. In an embodiment, shown in FIG. 6B, the sensor assembly 106 includes a plurality of strain gauges 500 arranged in series. In an embodiment, shown in FIG. 6C, the sensor assembly 106 includes a plurality of strain gauges 500 arranged in parallel. In an embodiment, shown in FIG. 6D, the sensor assembly 106 includes an array 602 of strain gauges 500. The array 602 of strain gauges can facilitate the monitoring of strain of the textile 104 across multiple axes, such as across a width of the textile 104, across a length of the textile 104, or the like.

The circuitry 108 is operably coupled to the sensor assembly 106 and is configured to receive one or more sense signals associated with the strain of the textile 104 from the sensor assembly 106. For example, in an embodiment, one or more strain gauges 500 monitor the textile 104 of a compression bandage to determine one or more strains associated with the textile 104, whereby an output of the one or more strain gauges 500 includes one or more sense signals associated with the one or more strains associated with the textile. The circuitry 108 includes components to process the one or more sense signals from the sensor assembly 106 and to provide instruction to the reporter 110 to generate one or more communication signals associated with the strain of the textile 104, determinations made by the circuitry 108, or other information. For example, the circuitry 108 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an embodiment, the circuitry 108 includes one or more ASICs having a plurality of predefined logic components. In an embodiment, the circuitry 108 includes one or more FPGAs having a plurality of programmable logic commands.

The circuitry 108 is configured to receive the one or more sense signals from the sensor assembly (e.g., a strain gauge 500) associated with the strain of the textile 104 and can provide analysis of the one or more sense signals. For example, in an embodiment, the circuitry 108 is configured to determine whether the strain of the textile 104 is less than a threshold strain value. The threshold strain value can correspond to a desired pressure applied by the textile 104 of a compression bandage to the body portion of the individual, such as to treat edema, lymphedema, venous conditions, or the like. For example, in an embodiment, the threshold strain value can be a strain of the textile 104 such that the textile 104 applies a pressure to the body portion of the individual from about 8 mmHg (millimeters of Mercury) to about 50 mmHg. When the strain of the textile 104 is less than the threshold strain value, this can indicate that the compression bandage is not applied properly to the body portion, or that the material of the compression bandage is beginning to wear, deteriorate, or over-stretch, which can indicate a need to re-apply the bandage to attain a desired pressure applied by the textile 104 to the body portion or replace the textile 104 with new material. The amount of tension of the textile 104 required to provide the desired application of pressure to the body portion (e.g., correlated with corresponding strain of the textile 104) can vary depending on the location of the body portion, the type of material comprising the textile 104, the weave pattern or fiber type of the textile 104, or so forth. In general, the pressure exerted by the textile 104 at application of the textile 104 to the body portion is a function of the tension in the fabric or material of the textile 104 (which can depend on the elastomeric properties), the number of layers applied, and the radius of the curvature of the body portion. The Laplace equation can be used to predict sub-bandage pressure by relating the tension, layers, and radius of curvature in a manner where the sub-bandage pressure is directly proportional to bandage tension, and inversely proportional to the radius of curvature of the body portion to which the textile 104 is applied. For example, in an embodiment, the pressure exerted by the textile 104 can be calculated by the following:

$$\text{Pressure} = \frac{\text{Tension} * n}{\text{Radius} * (\text{Textile Width})} \quad (1)$$

where n is the number of layers of the textile 104 applied, the radius is the radius of curvature of the body portion, and the textile width refers to the width of the textile 104 as applied (e.g., if the width of the material narrows as the textile 104 is tensioned as applied, the narrower width is used). An alternative equation can be provided by the following:

$$\text{Pressure} = \frac{\text{Tension} * n * K}{\text{Circumference} * (\text{Textile Width})} \quad (2)$$

where n is the number of layers of the textile 104 applied, K is a constant that can relate particular units of measurement, the circumference is the circumference of the body portion, and the textile width refers to the width of the textile 104 as applied.

In an embodiment, the circuitry 108 is configured to determine whether the strain of the textile 104 is equal to the threshold strain value. When the strain of the textile 104 is equal to the threshold strain value, this can indicate that the compression bandage system 100 is operating to produce a desired pressure to the body portion. In an embodiment, the circuitry 108 is configured to determine whether the strain of the textile 104 is greater than a threshold strain value. When the strain of the textile 104 is greater than the threshold strain value, this can indicate that the compression bandage may have been applied too tightly to the body portion or may have become too tight to apply the desired pressure to the body portion, resulting in a greater than desired pressure being applied to the body portion. When the pressure applied to the body portion becomes too high, the individual may be at risk for dangerous blood flow restrictions, or other conditions.

Figure 7:
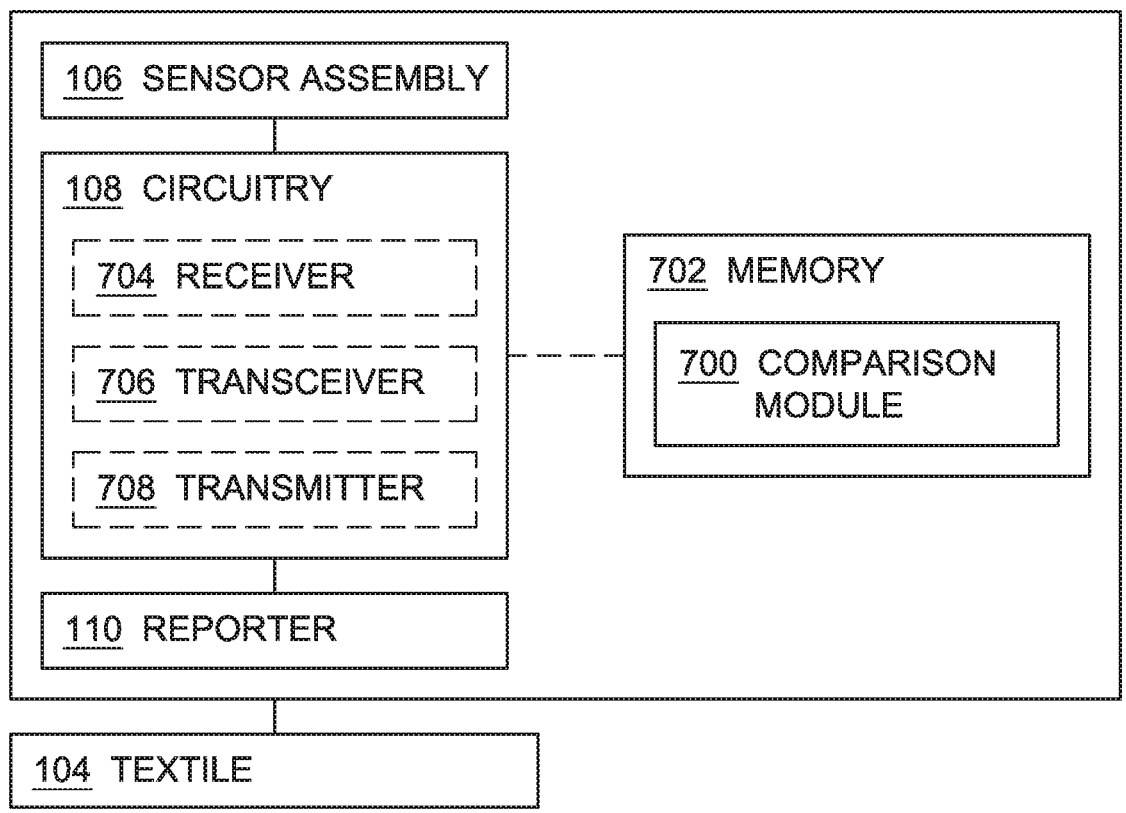
FIG. 7 is a schematic of an embodiment of a system such as shown in FIG. 1.

In an embodiment, shown in FIG. 7, the compression bandage system 100 includes a comparison module 700 accessible by, or integral with, the circuitry 108 to compare the strain of the textile 104 to reference data by comparing one or more sense signals generated by the sensor assembly 106 to reference data. The reference data can include, but is not limited to data associated with one or more of characteristics of a textile material including, but not limited to, thread or fiber tensile strength reference data, thread or fiber strain reference data, thread or fiber elastomeric property reference data, or so forth. For example, the reference data can include data indicative of the threshold strain value, where the comparison module 700 can compare the one or more sense signals generated by the sensor assembly 106 to the reference data to determine whether the strain of the textile 400 is less than, equal to, or greater than the threshold strain value. In embodiments, the circuitry 108 accesses the comparison module 700 by accessing a computer memory 702, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 700 and which can be accessed by the circuitry 108 or other associated accessing device. The reference data may be stored by the computer memory 702 of the compression bandage system 100, can be accessible by the circuitry 108 via wireless means, or can be available to the circuitry 108 through another method, such as through a remote network, a cloud network, and so forth. For example, the circuitry 108 can include a receiver 704 or transceiver 706 (e.g., antenna, etc.) to receive the reference data information or other information (e.g., strain threshold information, programming information) to facilitate operation or control of the compression bandage system 100 through wireless or wired communication protocols. In embodiments, the circuitry 108 can also include a transmitter 708 or transceiver 706 (e.g., antenna, etc.) to send information from the compression bandage system 100 through wireless or wired communication protocols, such as to communicate with an external device (e.g., external device 910 described herein). Such communication can include, for example, indications that the circuitry 108 is accessing one or more databases or memory devices storing reference data, computational protocols, system updates, or the like. By implementing the protocols of the comparison module 700, the circuitry 108 may compare the data obtained by the sensor assembly 106 (e.g., from strain sensor 500) pertaining to strain of the textile 104 to the reference data to determine whether the textile 104 is experiencing or has experienced a strain that is less than, equal to, or greater than the threshold strain value, or is experiencing or has experienced a strain that indicates that the textile 104 should be adjusted in some manner (e.g., reapplied to the body portion, replacement, refurbishing, etc.).

Figure 8:
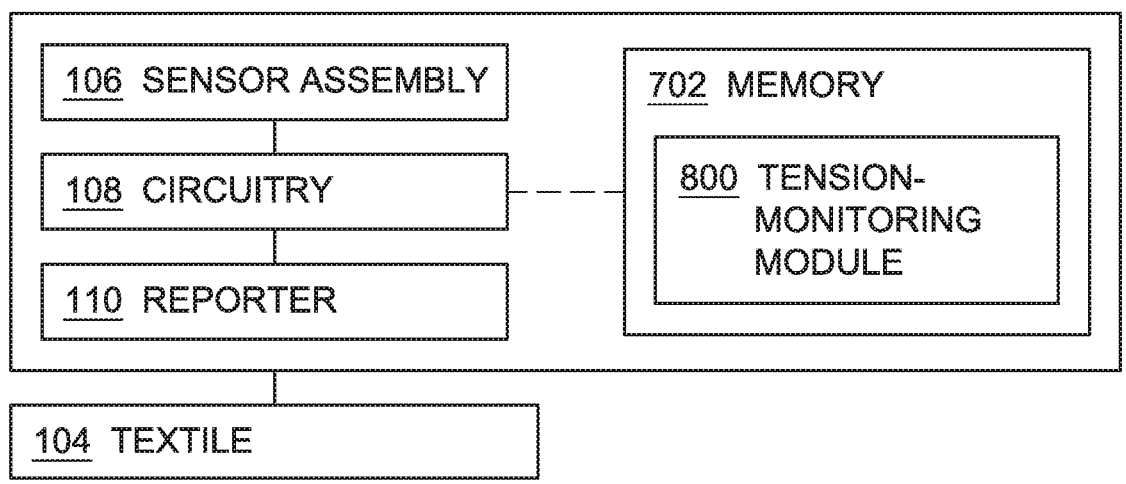
FIG. 8 is a schematic of an embodiment of a system such as shown in FIG. 1.

In an embodiment, shown in FIG. 8, the compression bandage system 100 includes a tension-monitoring module 800 accessible by, or integral with, the circuitry 108 to monitor a tension or strain of the textile 104, such as to provide monitoring of one or more of a tension or strain of the textile 104 over a time period, a tension or strain of the textile 104 over different locations/positions of the textile 104, or the like. For example, in an embodiment, the tension-monitoring module 800 includes protocols to compare the one or more sense signals generated by the sensor assembly 106 at a first time to the one or more sense signals generated by the sensor assembly 106 at a second time to provide analysis of the strain of the textile 104 over a period of time. By analyzing the strain of the textile 104 over a period of time, the compression bandage system 100 can be monitored to determine whether the textile 104 is beginning to lose pressure against the body portion, whether the textile 104 is increasing the pressure applied to the body portion over time, whether the textile 104 is undergoing a temporal characteristic change (e.g., degradation of material), or the like. In an embodiment, the tension-monitoring module 800 includes protocols to compare the one or more sense signals generated by one or more strain sensors 500 of the sensor assembly 106 at a first location of the textile 104 to the one or more sense signals generated by one or more strain sensors 500 of the sensor assembly 106 at a second location of the textile 104. For example, the compression bandage system 100 can monitor strains associated with the textile 104 at different locations of the textile 104, such as to compare strains associated with a first location of the textile 104 to strains associated with the textile 104 at a second location. Such monitoring can facilitate determining whether the strain of the textile 104 at a particular location is too high, too low, etc. as compared to the strain of the textile 104 at another location, whether a strain at one location is changing as compared to a strain at another location, whether a desired gradient compression is being maintained, or the like.

Figure 9:
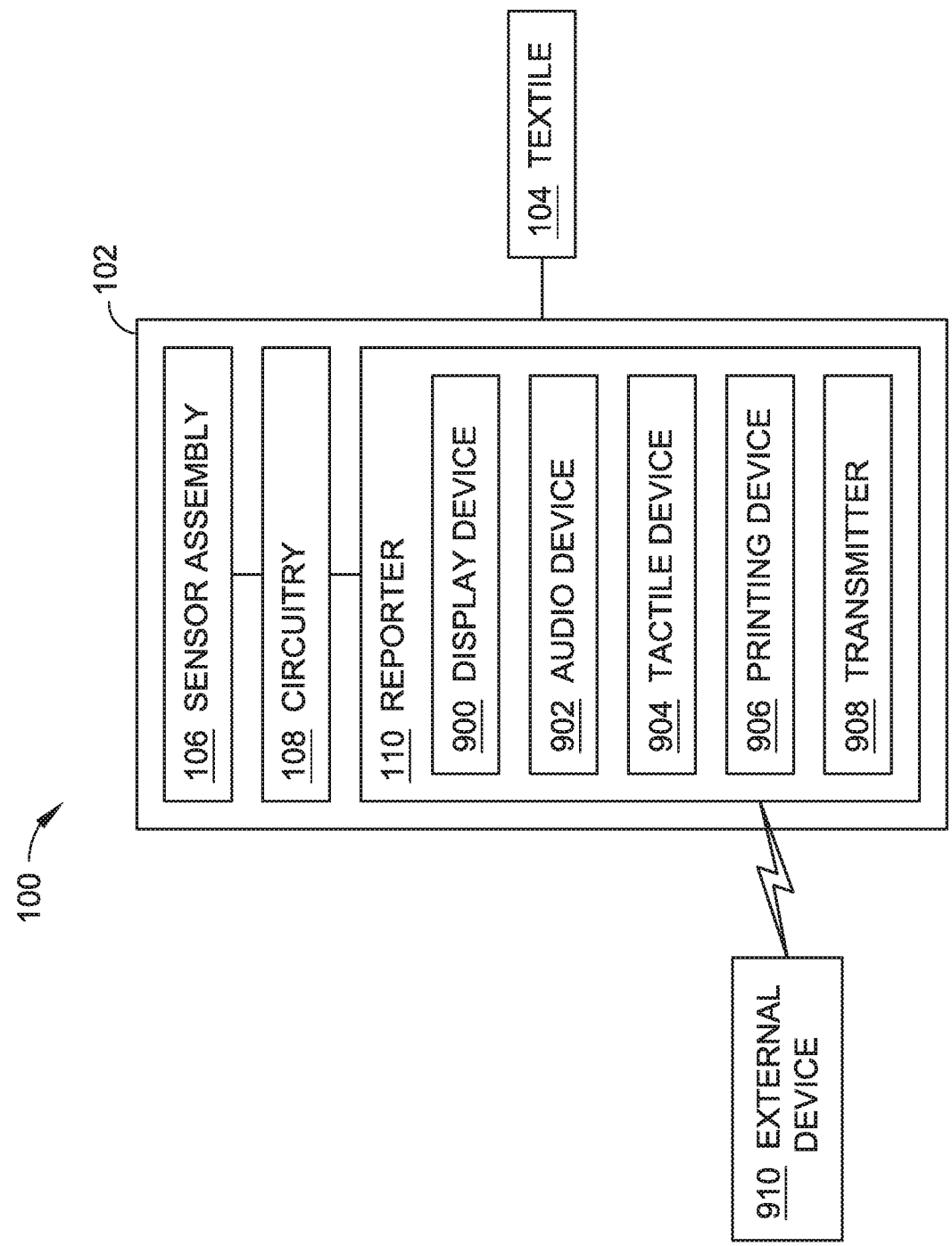
FIG. 9 is a schematic of an embodiment of a system such as shown in FIG. 1.

The reporter 110 is configured to generate one or more communication signals to report information associated with operation of the compression bandage system 100. In an embodiment, the reporter 110 is operably coupled to the circuitry 108 and configured to generate one or more communication signals responsive to instruction by the circuitry 108, where the one or more communication signals are associated with the strain of the textile 104. The information from the reporter 110 can be provided one or more of visually (e.g., via transmission, printing information, or display of visual information), audibly (e.g., via transmission or display of auditory information), tactually (e.g., via presentation of tactile information), or as data (e.g., via transmission or display of one or more data signals associated with the information to convey). The reporter 110 may function in combination with the circuitry 108 to provide visual, auditory, or tactile information associated with the strain of the textile 104, such as quantitative strain measurements or analyses, qualitative strain measurements or analyses, comparative strain measurements or analyses, or the like. In an embodiment, shown in FIG. 9, the reporter 110 includes a display device 900 configured to report, communicate, or otherwise provide information to a user of the compression bandage system 100, such as to provide visual (e.g., graphical, textual, etc.) indications of the information associated with operation of the compression bandage system 100. The display device 900 can include, but is not limited to, one or more of a graphical user interface (GUI), a touchscreen assembly (e.g., a capacitive touch screen), a liquid crystal display (LCD), a light-emitting diode (LED) display, or a projection-based display. In an embodiment, the reporter 110 is operably coupled to a display device remote from the reporter 110. As shown in FIG. 9, the reporter 110 can include one or more of an audio device 902 (e.g., an alarm device), configured to provide auditory indications of the information associated with operation of the compression bandage system 100; a tactile device 904 (e.g., a vibration device), configured to provide tactile indications of the information associated with operation of the compression bandage system 100; a printing device 906, configured to print a tangible/physical indication of the information associated with operation of the compression bandage system 100; or a transmitter 908, configured to transmit information from the compression bandage system 100 to an external device 910 or location (e.g., a remote entity, a remote device (e.g., a device accessible by the individual or a caretaker, a device accessible by a healthcare provider, digital health record database(s), a third party computing device, an alarm, or so forth), a remote server, a remote network (e.g., a LAN (local area network), a BAN (body area network), a smart house, or so forth), an external device associated with an external network that includes one or more of a health provider network, an insurance network, a personal health record, or a personal health database, or so forth). In an embodiment, one or more of the audio device 902, the tactile device 904, printing device 906, or the transmitter 908 can be operably coupled to the reporter 110, where the reporter 110 can communicate with the respective devices, such as through a communications antenna, or the like. The external device 910 can include a communication device, such as one or more of a mobile communication device or a computer system including, but not limited to, one or more mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The reporter 110 can communicate (e.g., send and receive communication signals) with the external device 910 via one or more connected and wireless communication mechanisms including, but not limited to acoustic communication signals, optical communication signals, radio communication signals, infrared communication signals, ultrasonic communication signals, and the like. In an embodiment, one or more of the sensor assembly 106 or the circuitry 108 can receive communication signals from the external device 910. For example, the external device 910 (e.g., a cellular or network-based device) can transmit one or more communication signals to one or more of the sensor assembly 106 or the circuitry 108, where such communication signals can initiate or terminate particular functionalities of the sensor assembly 106 or circuitry 108 (e.g., turn on/off), provide programming information, provide updated functionalities, provide or update strain threshold values or reference data, or the like. In an embodiment, the circuitry 108 directs the reporter 110 to generate the one or more communication signals associated with the strain of the textile 104 responsive to a query from the external device 910.

Figure 10:
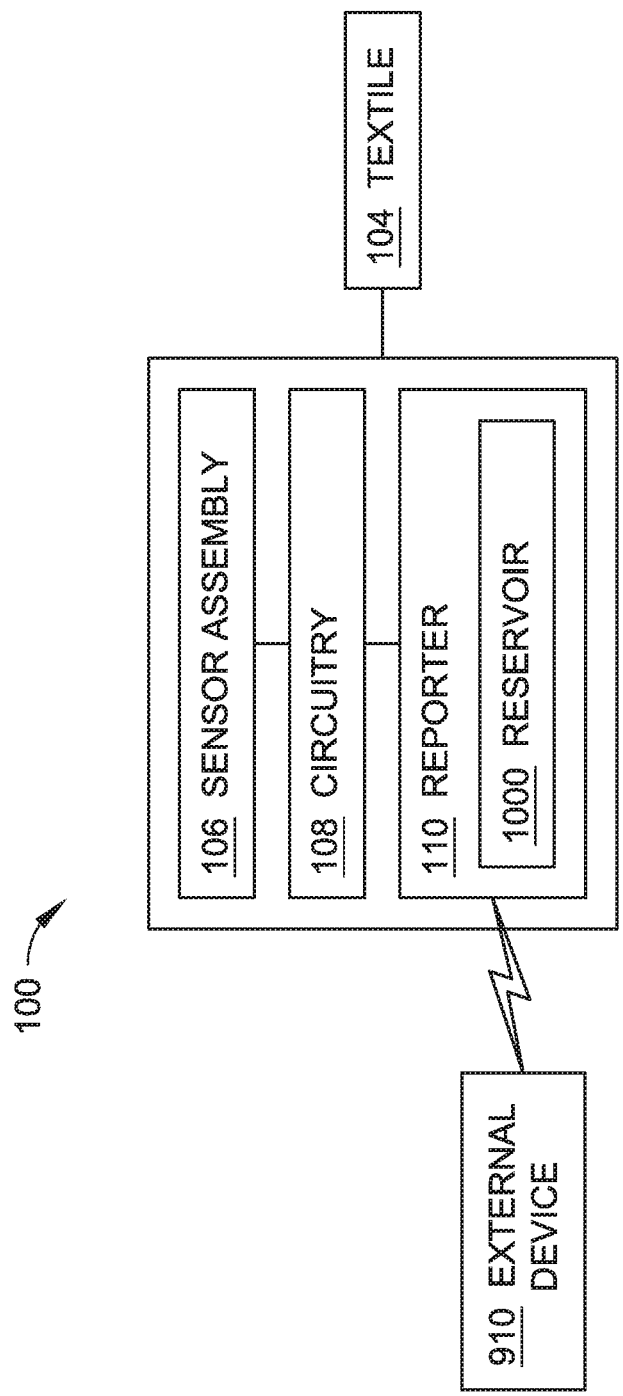
FIG. 10 is a schematic of an embodiment of a system such as shown in FIG. 1.

The reporter 110 can be configured to provide a visual indication pertaining to one or more sense signals associated with the strain of the textile 104 provided by the sensor assembly 106. In an embodiment, shown in FIG. 10, the reporter includes a reservoir 1000 having a fluid stored therein. The reporter 110 can actuate the reservoir 1000 to release the fluid responsive to instruction by the circuitry 108. For example, when the circuitry 108 determines, via the comparison module 700, the tension-monitoring module 800, or other determination process, that the strain of the textile 104 is outside of a desired parameter (e.g., strain higher than a threshold strain, strain lower than a threshold strain, etc.), the circuitry 108 can send one or more actuation signals to the reservoir 1000 to release the fluid stored therein. The fluid can release from the reservoir 1000 onto at least a portion of the textile 104 to provide a visual indication of the actuation by the circuitry 108. In an embodiment the fluid includes a dye to provide a readily identifiable color or pattern associated with release of the fluid from the reservoir 1000.

In an embodiment, the one or more sense signals generated by the sensor assembly 106 (e.g., via a strain gauge 500) can provide a quantitative strain value for the textile 104. For example, the circuitry 108 can direct the display device 900 to provide an indication of the quantitative strain value for the textile 104, can direct the printing device to print a document or article to provide the quantitative strain value for the textile 104, can direct the transmitter 908 to transmit data associated with the quantitative strain value for the textile 104, or the like. In an embodiment, the one or more sense signals generated by the sensor assembly 106 (e.g., via a strain gauge 500) can provide a qualitative indication of the strain value for the textile 104. For example, the circuitry 108 can direct the tactile device 904 to vibrate when the strain of the textile 104 is within a certain range, can direct the reservoir 1000 to release the fluid when the strain of the textile 104 is within a certain range, or the like.

Figure 11A:
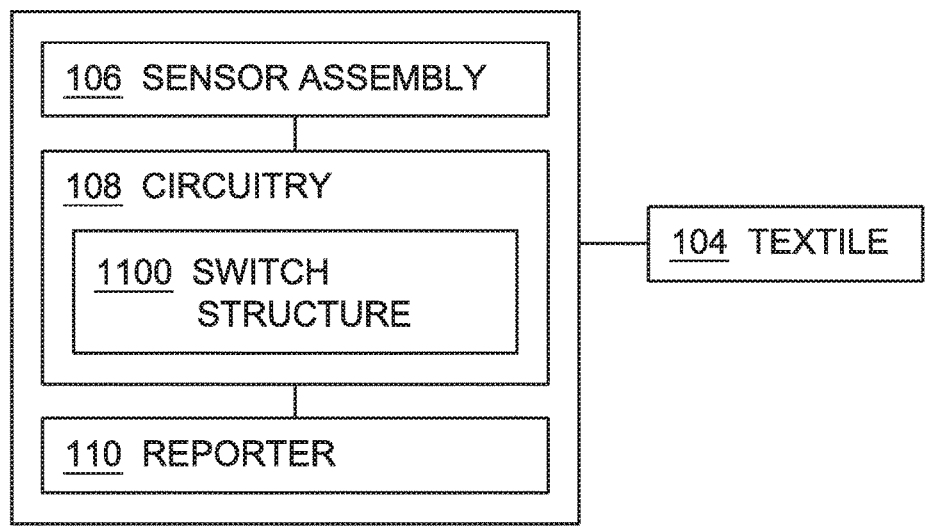
FIG. 11A is a schematic of an embodiment of a system such as shown in FIG. 1.

The circuitry 108 can be configured to activate the sensor assembly 108 at an activation strain threshold value of the textile 104. For example, the sensor assembly 106 can remain in a dormant or inactive state while the compression bandage system 100 is in storage or not otherwise disposed on a body portion of the individual. When the textile 104 is applied to the body portion, the strain of the textile 104 experienced during such application can cause the circuitry 108 to activate the sensor assembly 108 to activate and begin measuring the strain associated with the textile 104. For example, in an embodiment, shown in FIG. 11A, the circuitry 108 includes a switch structure 1100 switchable between an active configuration and an inactive configuration responsive to a strain of the textile 104. The switch structure 1100 can automatically provide power to the sensor assembly 106 (e.g., by closing a break in an electrical circuit providing power to the sensor assembly 106) when the strain of the textile 104 transitions the switch structure 1100 from the inactive configuration to the active configuration. When the textile 104 is removed from the body portion, the switch structure 1100 can transition back to the inactive configuration, due to change in the strain of the textile 104, where the switch structure 1100 can decouple the sensor assembly 106 from a power source (e.g., provide a break in the electrical circuitry providing power to the sensor assembly 106), to inactivate the sensor assembly 106, such as during a storage period, a repair period, or the like. In an embodiment, the activation strain threshold value of the textile 104 is a strain of the textile 104 corresponding to an applied pressure to the body portion from about 8 mmHg to about 50 mmHg. In an embodiment, the switch structure 1100 can be manually toggled to activate or deactivate one or more components or functionalities of the compression bandage system 100. For example, the switch structure 1100 can be manually toggled between the active configuration and an inactive configuration by a user, by an external device, or the like.

Figure 11B:
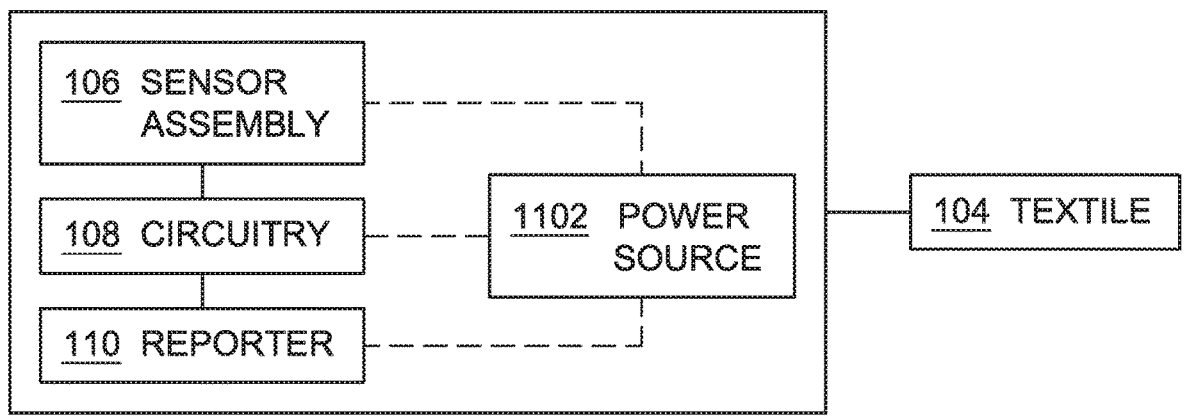
FIG. 11B is a schematic of an embodiment of a system such as shown in FIG. 1.

In an embodiment, shown in FIG. 11B, the compression bandage system 100 includes at least one power source 1102 operably coupled with at least one of the sensor assembly 106, the circuitry 108, or the reporter 110. For example, the power source 1102 can include a battery, microbattery, or thin-film battery. For example, the power source 1102 can include an energy harvester (e.g., an inductive coil or near field communication source) that can harvest energy from an outside source, for example an external device (such as external device 910). In an embodiment, the power source 1102 includes stretchable or flexible electronics. For example, the power source 1102 can include a silicon filamentary serpentine-shaped photovoltaic cell. For example, the power source 1102 can include filamentary serpentine-shaped inductive coils, e.g., as a component of a multifunctional unit as described herein.

Figure 12:
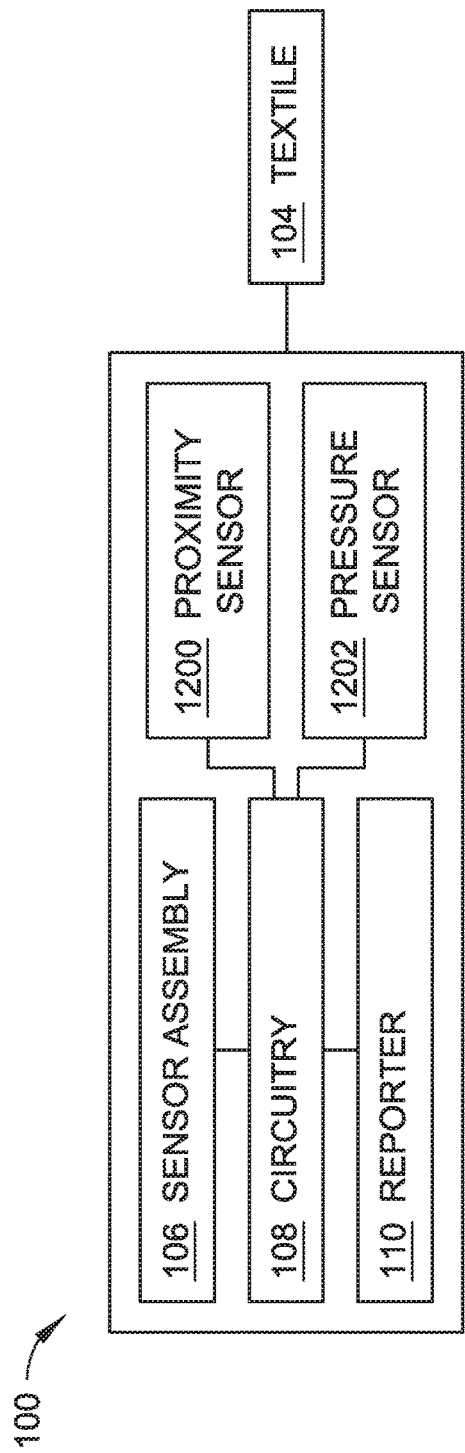
FIG. 12 is a schematic of an embodiment of a system such as shown in FIG. 1.

In an embodiment, shown in FIG. 12, the compression bandage system 100 includes one or more of a proximity sensor 1200 or a pressure sensor 1202 coupled to the deformable substrate 102. The proximity sensor 1200 is configured to generate one or more sense signals associated with at least one of detection of an external object in contact with the textile 104 or absence of detection of an external object in contact with the textile 104. For example, the proximity sensor 1200 can monitor an area around the textile 104 to determine whether an external object is near the textile 104, which can potentially influence a strain of the textile 104 if the textile 104 and the external object interact. The external object can include, but is not limited to, a floor surface, a wall surface, a desk surface, a furniture surface, an item located on a floor surface, an item located on the floor surface, an item located on the wall surface, an item located on the desk surface, an item located on the furniture surface or the like. The proximity sensor 1200 can include one or more of an optical proximity sensor, an acoustic proximity sensor, or an electromagnetic proximity sensor. The optical proximity sensor, the acoustic proximity sensor, and the electromagnetic proximity sensor can be configured to emit signals and detect reflected signals in accordance with their specific detection protocols. An optical proximity sensor can detect one or more optical signals (e.g., one or more optical electromagnetic signals) and generate one or more sense signals in response thereto. For example, an optical proximity sensor can be configured to detect and/or identify an external object and its proximity relative to the textile 104 based on detected optical signals. The optical sensor can include, but is not limited to, a photodetector (e.g., to detect one or more electromagnetic signals reflected from a surface of an object), an imaging device (e.g., a camera to generate a visual image of one or more objects in proximity to components of the compression bandage system 100), or the like. For example, an optical proximity sensor can be configured to emit a light signal and detect a reflected light signal, for example a reflected light signal that is reflected by the external object. The acoustic proximity sensor can detect and/or identify objects and their proximity relative to the textile 104 based on detected acoustic signals. For example, an acoustic proximity sensor can be configured to emit an acoustic signal and detect a reflected signal, for example a reflected acoustic signal that is reflected by an external object. The acoustic proximity sensor can include, but is not limited to, sensors configured to detect ultrasonic signals, radio-frequency signals, or the like.

An electromagnetic proximity sensor can detect and/or identify objects and their proximity relative to components of the compression bandage system 100 based on detected electromagnetic signals. For example, an electromagnetic proximity sensor can be configured to detect and/or identify an external device and its proximity relative to the textile 104 based on detected electromagnetic signals. For example, an electromagnetic proximity sensor can be configured to emit an electromagnetic signal and detect a reflected electromagnetic signal, for example a reflected electromagnetic signal that is reflected by the external device. The electromagnetic proximity sensor can include, for example, a bolometer or a thermal imaging device (e.g., to measure incident electromagnetic radiation of objects in proximity to the textile 104). The pressure sensor 1202 can be configured to sense a direct impact with an object, such as an impact between the external object and the textile 104. In an embodiment, the circuitry 108 receives the one or more sense signals from one or more of the proximity sensor 1200 or the pressure sensor 1202 for processing and/or instructing the reporter 110 to generate one or more communication signals associated with the one or more sense signals from one or more of the proximity sensor 1200 or the pressure sensor 1202. For example, the one or more sense signals from one or more of the proximity sensor 1200 or the pressure sensor 1202 can facilitate determining whether a current or future strain experienced by the textile 104 is associated with an impact or future impact with an external object, as differentiated from a strain of the textile 104 associated with wear and tear, positioning, or the like. The proximity sensor 1200 and the pressure sensor 1202 can be components of the sensor assembly 106 or can be separate sensors coupled to the deformable substrate 102.

Figure 13:
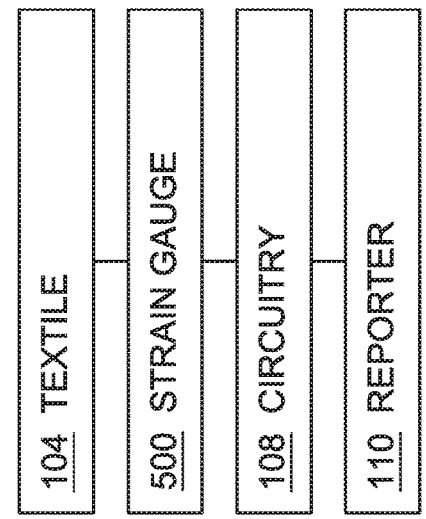
FIG. 13 is a schematic of a compression bandage system for monitoring compression applied by a compression bandage having stretchable electronics integrated therewith.

In an embodiment, shown in FIG. 13, the compression bandage system 100 is configured to include the textile 104, one or more strain gauges 500, the circuitry 108, and the reporter 110. The textile 104 is configured to conform to a body portion of an individual subject, where the one or more strain gauges 500 are integrated with the textile 104 and configured to generate one or more sense signals associated with a strain of the textile 104. The circuitry is operably coupled to the one or more strain gauges 500 and configured to receive the one or more sense signals associated with the strain of the textile 104. The reporter 110 is operably coupled to the circuitry 108 and configured to generate one or more communication signals responsive to instruction by the circuitry 108. The one or more communication signals are associated with the strain of the textile 104 (e.g., as measured by the one or more strain gauges 500). The circuitry 108 is configured to instruct the reporter 110 to generate the one or more communication signals when the strain of the textile 104 is less than a threshold strain value. As described herein, the threshold strain value can correspond to a desired pressure applied by the textile 104 of a compression bandage to the body portion of the individual.

Figure 14:
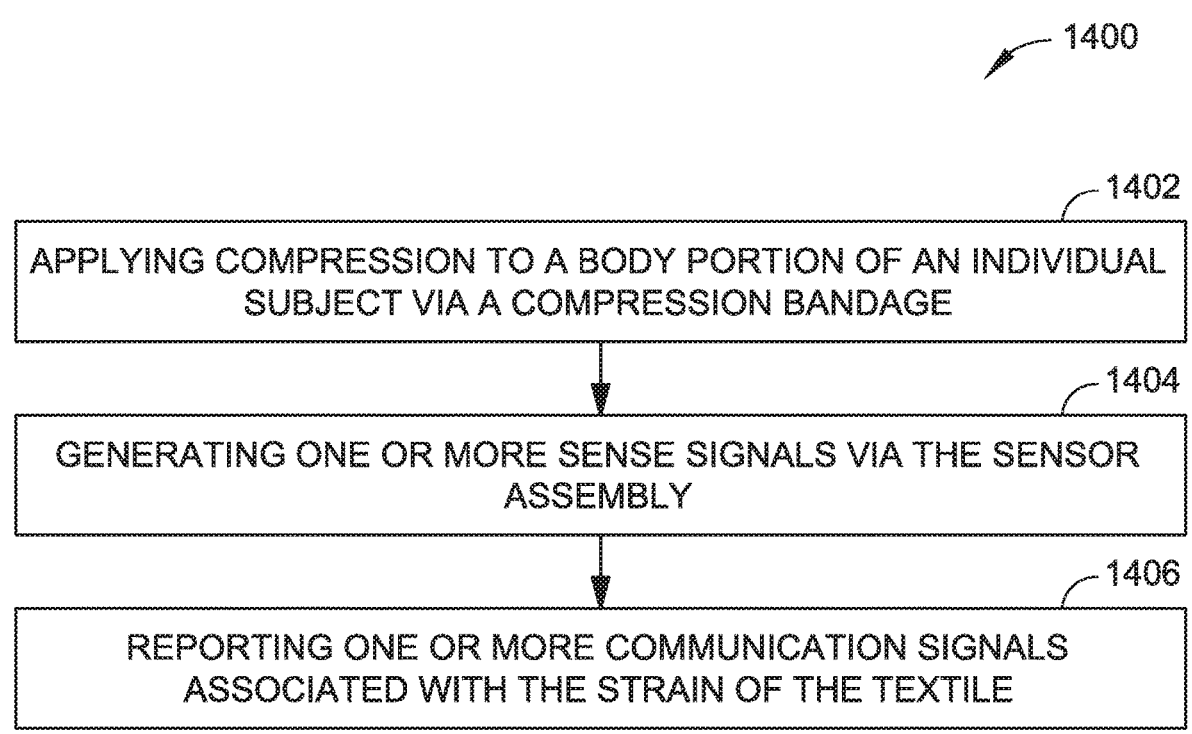
FIG. 14 is a flowchart of a method of monitoring compression applied by a compression bandage having stretchable electronics integrated therewith.

FIG. 14 illustrates a method 1400 for monitoring compression applied by a compression bandage to a body portion of an individual, which can result in generating notifications associated with conditions of the compression bandage during use. Method 1400 shows applying compression to a body portion of an individual subject via a compression bandage in block 1402, where the compression bandage includes a textile having a sensor assembly integrated therewith. For example, a compression bandage fabricated from textile 104 can be applied to a body portion (e.g., ankle region 200, a leg, a knee, a foot, an arm, an elbow, a hand, a wrist, a torso, a neck, or other body portion) of an individual subject, where the textile 104 includes the sensor assembly 106 integrated therewith. Method 1400 also includes generating one or more sense signals via the sensor assembly in block 1404, where the one or more sense signals are associated with a strain of the textile. For example, the sensor assembly 106 can monitor the textile 104 to sense or detect a strain of the textile 104 and generate the one or more sense signals responsive thereto. Method 1400 further includes reporting one or more communication signals associated with the strain of the textile in block 1406. For example, the circuitry 108 can be coupled to the sensor assembly 106 and direct the reporter 110 to generate the one or more communication signals. The circuitry 108 can direct the reporter 110 to generate the one or more communication signals according to circumstances including, but not limited to, a comparison of the one or more sense signals with reference data (e.g., via comparison module 700), an analysis of the one or more sense signals (e.g., via tension-monitoring module 800, etc.), a query received from an external device (e.g., external device 910), or the like. The one or more communication signals can be involved in reporting protocols including, but not limited to, visual reporting (e.g., via display device 900, printing device 906, reservoir 1000, etc.), auditory reporting (e.g., via audio device 902), tactile reporting (e.g., via tactile device 904), or data or signal reporting (e.g., via transmitter 908).

Figure 15:
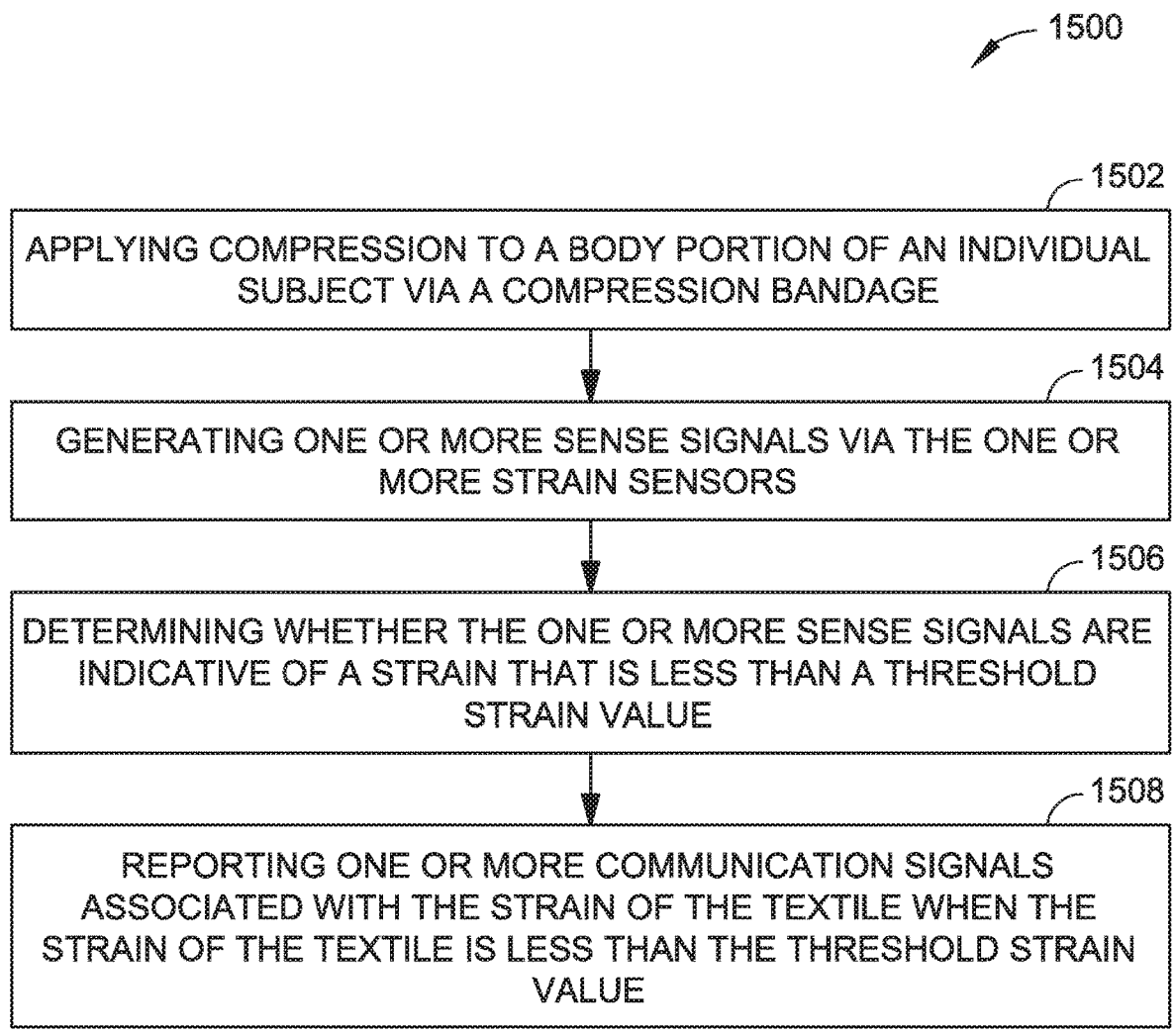
FIG. 15 is a flowchart of a method of monitoring compression applied by a compression bandage having stretchable electronics integrated therewith.

FIG. 15 illustrates a method 1500 for monitoring compression applied by a compression bandage to a body portion of an individual, which can result in generating notifications associated with conditions of the compression bandage during use. Method 1500 shows applying compression to a body portion of an individual subject via a compression bandage in block 1502, where the compression bandage includes a textile having one or more strain sensors integrated therewith. For example, a compression bandage fabricated from textile 104 can be applied to a body portion (e.g., ankle region 200, a leg, a knee, a foot, an arm, an elbow, a hand, a wrist, a torso, a neck, or other body portion) of an individual subject, where the textile 104 includes one or more strain gauges 500 integrated therewith. Method 1500 also includes generating one or more sense signals via the one or more strain sensors in block 1504, where the one or more sense signals are associated with a strain of the textile. For example, the one or more strain gauges 500 can monitor the textile 104 to sense or detect a strain of the textile 104 and generate the one or more sense signals responsive thereto. Method 1500 also includes determining whether the one or more sense signals are indicative of a strain that is less than a threshold strain value in block 1506. For example, the circuitry 108 can determine whether the one or more sense signals from the one or more strain gauges 500 are indicative of a strain that is less than a threshold strain value, such as through analysis of the one or more sense signals via at least one of the comparison module 700, the tension-monitoring module 800, or the like. Method 1500 further includes reporting one or more communication signals associated with the strain of the textile when the strain of the textile is less than the threshold strain value in block 1408. For example, the circuitry 108 can be coupled to the one or more strain gauges 500 and direct the reporter 110 to generate the one or more communication signals when it is determined (e.g., via at least one of the comparison module 700, the tension-monitoring module 800, or the like) that the strain of the textile 104 is less than the threshold strain value. The one or more communication signals can be involved in reporting protocols including, but not limited to, visual reporting (e.g., via display device 900, printing device 906, reservoir 1000, etc.), auditory reporting (e.g., via audio device 902), tactile reporting (e.g., via tactile device 904), or data or signal reporting (e.g., via transmitter 908).

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the systems, devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of one or more of the systems described herein (e.g., compression bandage system 100) used to monitor compression applied by a compression bandage having stretchable electronics integrated therewith, and any associated computing devices of the system operate as specific use computers for purposes of the claimed system, and not general use computers. In embodiments, at least one associated computing device of the system operates as a specific use computer for purposes of the claimed system, and not a general use computer. In embodiments, at least one of the associated computing devices of the system is hardwired with a specific ROM to instruct the at least one computing device. In embodiments, one of skill in the art recognizes that the systems described herein (e.g., compression bandage system 100) and associated systems/devices effect an improvement at least in the technological field of compression bandage strain monitoring.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A compression bandage system, comprising:
   a deformable substrate integrated with a textile configured to conform to a body portion;
   a sensor assembly coupled to the deformable substrate, the sensor assembly including
      one or more strain gauges configured to generate one or more sense signals associated with a strain of the textile, and
      a proximity sensor coupled to the deformable substrate, the proximity sensor configured to generate one or more sense signals associated with detection of an external object in contact with the textile;
   circuitry operably coupled to the sensor assembly and configured to receive the one or more sense signals associated with the strain of the textile and the one or more sense signals associated with detection of the external object in contact with the textile, the circuitry including a tension-monitoring module configured to compare the one or more sense signals associated with the strain of the textile generated by the sensor assembly at a first time at a first location to the one or more sense signals associated with the strain of the textile generated by the sensor assembly at a second time at the first location and to compare the one or more sense signals associated with the strain of the textile generated by the sensor assembly at the first time at a second location to the one or more sense signals associated with the strain of the textile generated by the sensor assembly at the second time at the second location, and to determine how any changes in strain at the first location compare to any changes in strain at the second location; and
   a reporter operably coupled to the circuitry and configured to generate one or more communication signals responsive to a first instruction by the circuitry, the one or more communication signals associated with the strain of the textile, the reporter further configured to generate an additional communication signal responsive to a second instruction by the circuitry, the additional communication signal associated with the one or more sense signals associated with detection of the external object in contact with the textile generated by the proximity sensor.

2. The compression bandage system of claim 1, wherein the circuitry is configured to determine whether the strain of the textile is less than, equal to, or greater than a threshold strain value.

3. The compression bandage system of claim 2, wherein the circuitry includes a comparison module configured to compare the one or more sense signals generated by the sensor assembly to reference data indicative of the threshold strain value.

4. The compression bandage system of claim 1, wherein at least one of the circuitry or the reporter is configured to communicate with an external device.

5. The compression bandage system of claim 4, wherein at least one of the circuitry or the reporter is configured to receive one or more communication signals from the external device.

6. The compression bandage system of claim 5, wherein the circuitry is configured to instruct the reporter to generate the one or more communication signals associated with the strain of the textile responsive to query from the external device.

7. The compression bandage system of claim 1, wherein the circuitry is configured to activate the sensor assembly at an activation strain threshold value of the textile.

8. The compression bandage system of claim 7, wherein the activation strain threshold value of the textile is a strain of the textile sufficient to apply a pressure to the body portion from 8 mmHg to 50 mmHg.

9. The compression bandage system of claim 1, wherein the circuitry is configured to actuate the sensor assembly below an activation strain threshold value of the textile.

10. The compression bandage system of claim 1, wherein the circuitry is configured to disregard one or more sense signals associated with the strain of the textile upon receipt of the one or more sense signals associated with detection by the proximity sensor of the external object in contact with the textile.

11. The compression bandage system of claim 1, further including a pressure sensor coupled to the deformable substrate.

12. The compression bandage system of claim 1, wherein the one or more strain gauges include at least one of a metallic stack having a first metallic material layered on a second metallic material, a nanomembrane strain sensor, a piezoresistor strain sensor, a bonded metallic strain sensor having a metallic material arranged in a grid, a wave-structured strain sensor, an open-mesh structured strain sensor, or a plurality of metallic-coated nanofibers in an interlocked arrangement supported on a substrate layer.

13. The compression bandage system of claim 1, wherein at least a portion of the one or more strain gauges is at least one of embedded within the textile, woven into the textile, affixed to a surface of the textile, or printed directly onto a surface of the textile.

14. The compression bandage system of claim 1, wherein the sensor assembly includes at least one of a plurality of strain gauges or an array of strain gauges.

15. The compression bandage system of claim 1, wherein the reporter includes a reservoir having a fluid stored therein, and wherein the reporter is configured to actuate the reservoir to release the fluid onto at least a portion of the textile responsive to instruction by the circuitry, the fluid including a dye.

16. The compression bandage system of claim 1, wherein the proximity sensor includes at least one of an optical proximity sensor, an acoustic proximity sensor, or an electromagnetic proximity sensor.

17. The compression bandage system of claim 1, wherein the textile includes one or more conductive threads incorporating one or more conductive materials integrated within a weave pattern of the textile, the one or more conductive threads supporting transfer of electric transmissions between the textile and one or more components coupled to the deformable substrate.

18. A garment system, comprising:
a deformable substrate integrated with a textile of a garment configured to conform to a body portion;
a sensor assembly coupled to the deformable substrate, the sensor assembly including
one or more strain gauges configured to generate one or more sense signals associated with a strain of the textile, and
a proximity sensor coupled to the deformable substrate, the proximity sensor configured to generate one or more sense signals associated with detection of an external object in contact with the textile;
circuitry operably coupled to the sensor assembly and configured to receive the one or more sense signals associated with the strain of the textile and the one or more sense signals associated with detection of the external object in contact with the textile, the circuitry including a tension-monitoring module configured to compare the one or more sense signals associated with the strain of the textile generated by the sensor assembly at a first time at a first location to the one or more sense signals associated with the strain of the textile generated by the sensor assembly a second time at the first location and to compare the one or more sense signals associated with the strain of the textile generated by the sensor assembly at the first time at a second location to the one or more sense signals associated with the strain of the textile generated by the sensor assembly at the second time at the second location, and to determine how any changes in strain at the first location compare to any changes in strain at the second location; and
a reporter operably coupled to the circuitry and configured to generate one or more communication signals responsive to a first instruction by the circuitry, the one or more communication signals associated with the strain of the textile, the reporter further configured to generate an additional communication signal responsive to a second instruction by the circuitry, the additional communication signal associated with the one or more sense signals associated with detection of the external object in contact with the textile generated by the proximity sensor.

19. The garment system of claim 18, wherein the one or more strain gauges include at least one strain sensor having a piezoresistive material that includes a tapered portion at a midpoint of the piezoresistive material.

20. The garment system of claim 18, wherein the one or more strain gauges include at least one strain sensor having a stacked arrangement of titanium metal on gold metal, wherein the gold metal has a thickness greater than a thickness of the titanium metal.

* * * * *